(12) United States Patent
Kriz et al.

(10) Patent No.: US 7,683,237 B2
(45) Date of Patent: Mar. 23, 2010

(54) MAIZE SEED WITH SYNERGISTICALLY ENHANCED LYSINE CONTENT

(75) Inventors: Alan L. Kriz, Gales Ferry, CT (US); Shihshieh Huang, Stonington, CT (US); Michael H. Luethy, Webster Groves, MO (US)

(73) Assignee: Monsanto Technology LLC, St. Louis, MO (US)

( * ) Notice: Subject to any disclaimer, the term of this patent is extended or adjusted under 35 U.S.C. 154(b) by 231 days.

(21) Appl. No.: 11/077,089

(22) Filed: Mar. 10, 2005

(65) Prior Publication Data

US 2006/0064772 A1    Mar. 23, 2006

Related U.S. Application Data

(63) Continuation-in-part of application No. 11/057,062, filed on Feb. 10, 2005.

(60) Provisional application No. 60/543,157, filed on Feb. 10, 2004, provisional application No. 60/543,187, filed on Feb. 10, 2004, provisional application No. 60/600,859, filed on Aug. 11, 2004, provisional application No. 60/638,256, filed on Dec. 21, 2004.

(51) Int. Cl.
*A01H 1/00* (2006.01)
*C12N 15/82* (2006.01)
*C12N 15/87* (2006.01)
*C07H 21/04* (2006.01)

(52) U.S. Cl. .................. 800/278; 800/285; 800/286; 536/23.7

(58) Field of Classification Search ............ None
See application file for complete search history.

(56) References Cited

U.S. PATENT DOCUMENTS

| | | | |
|---|---|---|---|
| 5,107,065 A | 4/1992 | Shewmaker et al. | 800/298 |
| 5,231,020 A | 7/1993 | Jorgensen et al. | 800/281 |
| 5,258,300 A | 11/1993 | Glassman et al. | 800/288 |
| 5,283,184 A | 2/1994 | Jorgensen et al. | 800/285 |
| 5,508,468 A | 4/1996 | Lundquist et al. | 800/300.1 |
| 5,545,545 A | 8/1996 | Gengenbach et al. | 435/172.3 |
| 5,759,829 A | 6/1998 | Shewmaker et al. | 800/286 |
| 5,773,691 A * | 6/1998 | Falco et al. | 800/287 |
| 6,160,208 A | 12/2000 | Lundquist et al. | 800/320.1 |
| 6,326,193 B1 | 12/2001 | Liu et al. | 435/320.1 |
| 6,326,527 B1 * | 12/2001 | Kirihara et al. | 800/278 |
| 6,329,574 B1 * | 12/2001 | Lundquist et al. | 800/300.1 |
| 6,459,019 B1 | 10/2002 | Falco et al. | |
| 6,506,559 B1 | 1/2003 | Fire et al. | 435/6 |
| 6,777,589 B1 | 8/2004 | Lundquist et al. | 800/288 |
| 6,858,778 B1 | 2/2005 | Jung et al. | 800/298 |
| 2002/0013960 A1 | 1/2002 | Behr et al. | 800/320.1 |
| 2002/0048814 A1 | 4/2002 | Oeller | 435/455 |
| 2003/0018993 A1 | 1/2003 | Gutterson et al. | 800/286 |
| 2003/0036197 A1 | 2/2003 | Glassman et al. | 435/455 |
| 2003/0056242 A1 | 3/2003 | Falco et al. | |
| 2003/0175965 A1 | 9/2003 | Lowe et al. | 435/455 |
| 2004/0029283 A1 | 2/2004 | Fillatti | 435/468 |
| 2005/0176670 A1 | 8/2005 | Huang et al. | 514/44 |
| 2005/0193444 A1 | 9/2005 | Malvar et al. | 800/278 |
| 2006/0075515 A1 | 4/2006 | Luethy et al. | 800/278 |

FOREIGN PATENT DOCUMENTS

| | | |
|---|---|---|
| EP | 0426195 | 4/1994 |
| EP | 0462195 | 4/1994 |
| WO | WO 98/53083 | 11/1998 |
| WO | WO 99/53050 | 1/1999 |
| WO | WO 99/49029 | 9/1999 |

OTHER PUBLICATIONS

Kemper er al. 1999 The Plant Cell 11:1981-1993.*
Arruda et al. 2000 Trends in Plant Science 5:324-330.*
Wang et al. 2001 Plant Physiology 125:1766-1777.*
Huang et al. 2004, J. Agric. Food Chem. 52:1958-1964.*
Kemper et al. 1999 The Plant Cell 11:1981-1993.*
Bagga et al. 1997, The Plant Cell 9:1683-1696.*
Zhu et al. 2003 The Plant Cell 15:845-853.*
DeBuck et al., "Transgene silencing of invertedly repeated transgenes is released upon deletion of one of the transgenes involved," *Plant Mol. Biol.*, 46:433-445, 2001.
Jorgensen et al., "T-DNA is organized predominantly in inverted repeat structures in plants transformed with *Agrobacterium tumefaciens* C58 derivatives," *Mol. Gen. Genet.*, 207:471-477, 1987.
Mette et al., "Production of aberrant promoter transcripts contributes to methylation and silencing of unlinked homologous promoters in trans," *EMBO J.*, 18:241-248, 1999.
Mette et al., "Transcriptional silencing and promoter methylation triggered by double-stranded RNA," *EMBO J.*, 19:5194-5201, 2000.
Redenbaugh et al., "Safety Assessment of Genetically Engineered Flavr Savr™ Tomato", CRC Press, Inc. (1992), pp. 88-102.
Sanders at al., "Tomato transgene structure and silencing", *Nature Biotechnol.* 23:287-289, 2005.
Sijen at al., "RNA-mediated virus resistance: role of repeated transgenes and delineation of targeted regions," *Plant Cell*, 8:2277-2294, 1996.
Stam et al., "Post-transcriptional silencing of chalcone synthase in Petunia by inverted transgene repeats," *Plant J.*, 12:63-82, 1997.
PCT Search Report, App. No. PCT/US2006/008812, Sep. 29, 2006.
Ishida et al., "High efficiency transformation of maize (*zea mays* L.) mediated by *Agrobacterium tumefaciens*," *Nature Biotechnology*, 14:745-750, 1996.

(Continued)

*Primary Examiner*—Ashwin Mehta
*Assistant Examiner*—Li Zheng
(74) *Attorney, Agent, or Firm*—Chunping Li, Esq.; Sonnenschein Nath & Rosenthal LLP

(57) ABSTRACT

The present invention provides a transgenic maize plant having in its genome transgenic DNA including sequence for zein reduction and sequence for lysine biosynthesis, whereby expression of the transgenic DNA results in a synergistically increased lysine content of seed of the transgenic maize plant. The invention further provides a method for providing maize seed with synergistically increased lysine content.

8 Claims, 5 Drawing Sheets

OTHER PUBLICATIONS

Smith et al., "Gene expression—total silencing by intron-spliced hairpin RNAs," *Nature*, 407:319-320, 2000.

Waterhouse et al., "Virus resistance and gene silencing in plants can be induced by simultaneous expression of sense and antisense RNA," *Proc. Natl. Acad. Sci. USA*, 95:13959-13964, 1998.

Wesley et al., "Construct design for efficient, effective and high-throughput gene silencing in plants," *The Plant J.*, 27(6):581-590, 2001.

Wu et al., "Quantitative nature of the Prolamin-box, ACGT and AACA motifs in a rice glutelin gene promoter: minimal cis-element requirements for endosperm-specific gene expression," *The Plant J.*, 23(3):415-421, 2000.

Zhu et al., "A T-DNA insertion knockout of the bifunctional lysine-ketoglutarate reductase/saccharopine dehydrogenase gene elevates lysine levels in *Arabidopsis* seeds," *Plant Physiology*, 126:1539-1545, 2001.

U.S. Appl. No. 11/057,062, filed Aug. 11, 2005, Malvar et al.

U.S. Appl. No. 11/004,221, filed Jun. 16, 2005, Dizigan et al.

Huang et al., High lysine corn produced by the combination of enhanced lysine biosynthesis and reduced zein accumulation. XX pages. MS accepted for publication, J. Plant Biotechnology.

Huang et al. (2004) J. Agric. Food Chem., 52:1958-1964.

Huang et al. (2004) Transgenic Res., 13:451-461.

\* cited by examiner

C: Control recombinant CordapA from *E. coli*;
Em: Embryo; En: Endosperm

MAIZE SEED WITH SYNERGISTICALLY ENHANCED LYSINE CONTENT

This application is a Continuation-in-part of U.S. patent application Ser. No. 11/057,062 to Malvar et al., "Recombinant DNA for Gene Suppression", filed 10 Feb. 2005 and published as U.S. Patent Application Publication No. 2005/0176670A1, which claims priority under 35 U.S.C. 119(e) to U.S. Provisional Patent Application Nos. 60/543,157, filed 10 Feb. 2004, 60/543,187, filed Feb. 10, 2004, and 60/600,859, filed Aug. 11, 2004, the disclosures of all of which are incorporated by reference in their entireties herein. This application further claims benefit of priority to U.S. Provisional Patent Application No. 60/638,256 to Malvar et al., "Gene Suppression Using Introl-embedded DNA," filed 21 Dec. 2004, which is incorporated by reference in its entirety herein.

This application also incorporates by reference in its entirety herein the computer-readable sequence listing contained in the file named "53428B.ST25.txt", which is 21 kilobytes (measured in MS-Windows), was created on 9 Feb. 2005, and is located on a CD-ROM that was filed with U.S. patent application Ser. No. 11/057,062 to Malvar et al., "Recombinant DNA for Gene Suppression", on 10 Feb. 2005. This application further incorporates by reference in its entirety herein the computer-readable sequence listing contained in the file named "53429A.ST25.txt", which is 15 kilobytes (measured in MS-Windows), was created on 21 Dec. 2004, and is located on a CD-ROM that was filed with U.S. patent application No. 60/638,256 to Malvar et al., "Gene Suppression Using Intron-embedded DNA", on 21 Dec. 2004.

FIELD OF THE INVENTION

Disclosed herein are seeds for transgenic maize having elevated amino acid levels, particularly of lysine, recombinant DNA constructs for gene suppression, methods of making and using such constructs, and transgenic organisms, including plants, expressing such constructs.

BACKGROUND OF THE INVENTION

*Zea mays*, commonly known as maize or corn, is a grain important both as human food and as animal feed. Maize seeds or kernels are naturally low in lysine content due to its protein composition. The majority of maize seed proteins are the zeins or prolamins, which are found in the endosperm and account for more than half of the total seed proteins. Zeins or prolamins are rich in proline, alanine and glutamine, but almost completely devoid of the essential amino acids, lysine and tryptophan. Due to the relative abundance of zeins, the contribution of lysine and tryptophan from other seed proteins is diluted. Exogenous lysine is often added to animal feed as a necessary supplement. It is therefore of interest to increase the level of lysine in maize seed.

Amino acid levels in transgenic plants can be manipulated by various genetic techniques, including, but not limited to, modification of endogenous gene expression and/or expression of exogenous recombinant DNA in the transgenic plant. Coordinated decrease and increase of gene expression of more than one gene using transgenic constructs is disclosed in U.S. Patent Application Publication 2004/0126845. Methods and recombinant DNA constructs useful for producing antisense-oriented RNA for gene suppression in transgenic organisms are disclosed in U.S. patent application Ser. No. 11/057,062, published as U.S. Patent Application Publication No. 2005/0176670A1. U.S. Provisional Patent Application No. 60/638,256, discloses DNA cassettes for suppressing at least one gene in a cell of a eukaryote, such DNA cassettes comprising a promoter operably linked to transcribable DNA including at least an intron, a polyadenylation signal, and a polyadenylation site, where there is embedded in the intron heterologous DNA which is derived from at least one gene targeted for suppression and which is transcribable to RNA capable of suppressing the at least one gene. All of these referenced patent applications and publications are incorporated by reference in their entirety herein.

SUMMARY OF THE INVENTION

The present invention discloses a transgenic maize plant having in its genome transgenic DNA including sequence for zein reduction and sequence for lysine biosynthesis, whereby expression of the transgenic DNA results in a synergistically increased lysine content of seed of the transgenic maize plant. In one aspect of this invention, the sequence for zein reduction includes sequence for gene suppression of at least one zein synthesis gene. In another aspect of this invention, the sequence for lysine biosynthesis includes an exogenous lysine synthesis gene. In a further aspect of this invention, the sequence for lysine biosynthesis includes sequence for gene suppression of a lysine catabolic enzyme endogenous to the transgenic maize plant. Both primary transformed transgenic plants and their transgenic progeny are disclosed and claimed by the present invention.

The invention also provides a method for providing maize seed with synergistically increased lysine content, including:
  (a) providing a transgenic maize plant having in its genome transgenic DNA including sequence for zein reduction and sequence for lysine biosynthesis,
  (b) expressing the transgenic DNA in seed of the transgenic maize plant, the expressing resulting in a synergistically increased lysine content of the seed, and
  (c) harvesting the seed with synergistically increased lysine content.

Embodiments of the method of the invention include providing a transgenic maize plant by transformation, as well as providing a transgenic maize plant by genetic crossing techniques. Other specific embodiments of the invention are disclosed in the following detailed description.

BRIEF DESCRIPTION OF THE DRAWINGS

FIG. 2 depicts results of characterization assays of seed from M27908+.0028, representative of a second parent transgenic maize plant (M27908+) having in its genome transgenic DNA including sequence for lysine biosynthesis (cordapA), and seed from M27908-.0006, representative of the wild-type maize line M27908- which has a genotype substantially similar to M27908+ but lacks the sequence for lysine biosynthesis. See Example 1.

FIG. 5a shows correlation between free lysine and free aspartate. FIG. 5b shows correlation between free lysine and free asparagine. FIG. 5c shows correlation between free lysine and free glutamate. FIG. 5d shows correlation between free lysine and free saccharopine. FIG. 5e shows correlation between free lysine and CordapA expression. Each data point represents bulked ground ears harvested from a plot and two plots for each of the three F1s are used. Numbers within each graph correspond to $r^2$ values of linear regressions followed by significance levels (P).

DETAILED DESCRIPTION OF THE INVENTION

Figure 1A:
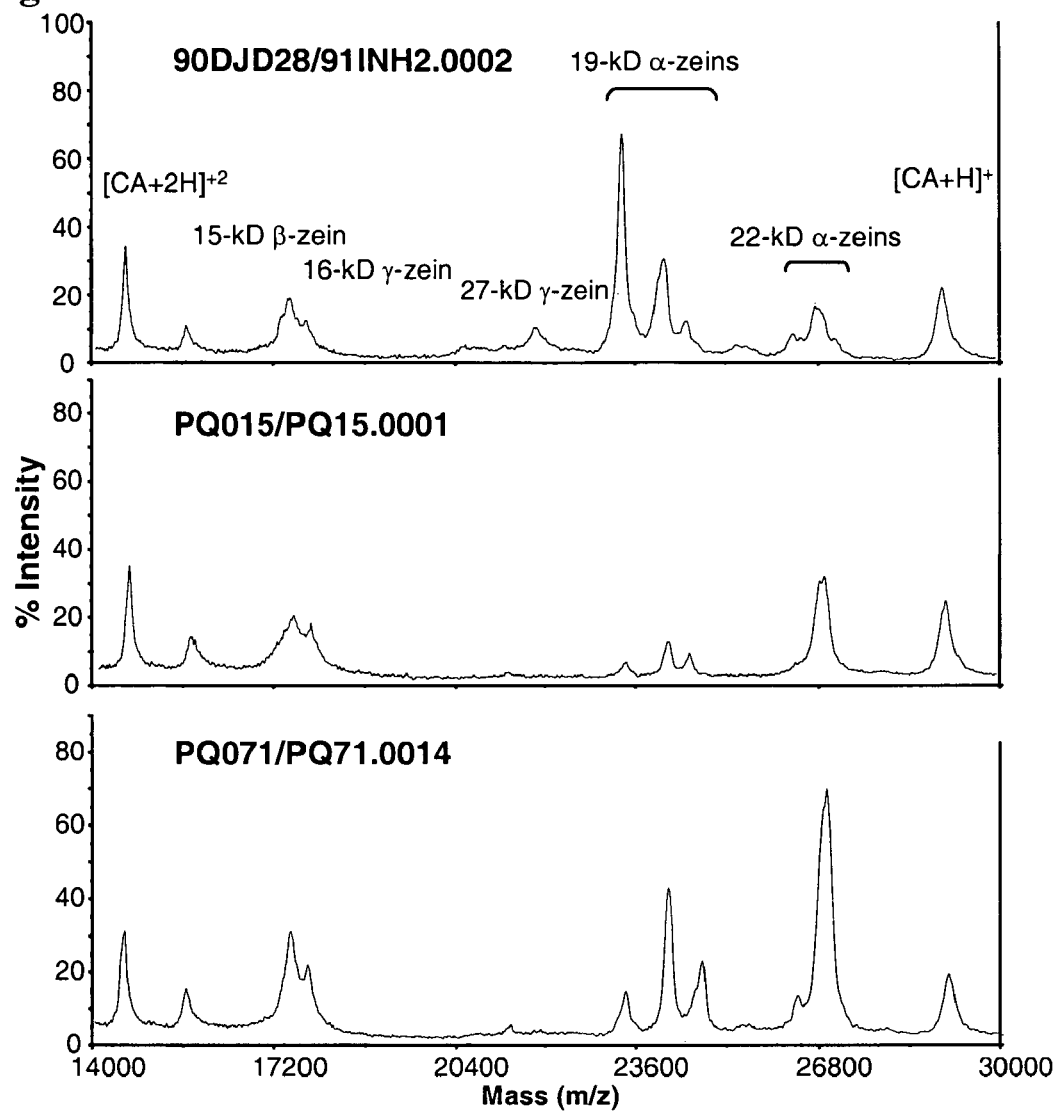
FIG. 1*a* depicts matrix-assisted laser desorption ionization time-of-flight mass spetra analyses of seed from first parent transgenic maize plants PQ015/PQ15.001 and PQ071/PQ71.0014, which have in their genome a sequence for zein reduction, showing the reduction in 19-kiloDalton alpha-zeins compared to the wild-type maize line 90DJD28/91INH2.0002 which has a genotype substantially similar to the first transgenic maize plants but lacks the sequence for zein reduction. See Example 1. X-axis is shown as m/z (mass to charge) ratios. Y-axis is shown as percent intensity. Mass spectra were normalized by a standard protein peak, [CA+H]$^+$ (carbonic anhydrase), near 29,000 m/z. The 15,615 Dalton peak between [CA+H]$^{2+}$ and 15-kiloDalton beta-zein was believed to be a contaminant from carbonic anhydrase.

Unless defined otherwise, all technical and scientific terms used herein have the same meaning as commonly understood by one of ordinary skill in the art to which this invention belongs. Generally, the nomenclature used herein and the manufacture or laboratory procedures described below are well known and commonly employed in the art. Conventional methods are used for these procedures, such as those provided in the art and various general references. Where a term is provided in the singular, the inventors also contemplate aspects of the invention described by the plural of that term. The nomenclature used herein and the laboratory procedures described below are those well known and commonly employed in the art. Where there are discrepancies in terms and definitions used in references that are incorporated by reference, the terms used in this application shall have the definitions given herein. Other technical terms used herein have their ordinary meaning in the art that they are used, as exemplified by a variety of technical dictionaries. The inventors do not intend to be limited to a mechanism or mode of action. Reference thereto is provided for illustrative purposes only.

Transgenic Plants

The present invention provides a transgenic maize plant having in its genome transgenic DNA including sequence for zein reduction and sequence for lysine biosynthesis, whereby expression of the transgenic DNA results in a synergistically increased lysine content of seed of the transgenic maize plant.

The transgenic DNA can be introduced into the genome of a maize plant by any one or more suitable means, including, but not limited to, direct delivery of DNA such as by PEG-mediated transformation of protoplasts, electroporation, agitation with silicon carbide fibers, *Agrobacterium*-mediated transformation, acceleration of DNA-coated particles, and other like methods known in the art. Maize cells, as well as those of virtually any other plant species, may be stably transformed by such methods, and these cells developed into transgenic plants of the invention. Preferred methods of plant transformation include, but are not limited to, microprojectile bombardment as illustrated, for example, in U.S. Pat. Nos. 5,015,580, 5,550,318, 5,538,880, 6,160,208, 6,399,861, and 6,403,865 and *Agrobacterium*-mediated transformation as illustrated, for example, in U.S. Pat. Nos. 5,635,055, 5,824, 877, 5,591,616, 5,981,840, and 6,384,301, all of which are incorporated by reference in their entirety herein.

The transgenic DNA includes sequence for zein reduction and sequence for lysine biosynthesis, which sequences are different from each other and can be introduced into the genome of the transgenic plant by means of one or more nucleic acid constructs (that is to say, introduced simultaneously in one construct or individually using more than one construct, separately or in parallel). Preferably, the sequence for zein reduction and sequence for lysine biosynthesis are expressed primarily in the seed of the transgenic plant, for example, by use of a seed-specific promoter in the construct or constructs, such as promoters from seed genes such as, but not limited to, napin (U.S. Pat. No. 5,420,034), maize L3 oleosin (U.S. Pat. No. 6,433,252), zein Z27 and glutelin 1 (Russell et al. (1997) *Transgenic Res.*, 6:157-166), globulin 1 (Belanger et al. (1991) *Genetics*, 129:863-872), and peroxiredoxin antioxidant (Per1) (Stacy et al. (1996) *Plant Mol Biol.*, 31:1205-1216), all of which are incorporated by reference herein. Expression of the transgenic DNA results in a synergistically increased lysine content of seed of the transgenic maize plant. The synergistically increased lysine content is an increase in the lysine content that is greater than the sum of the increase in lysine due to the individual effect of the sequence for zein reduction and the increase in lysine due to the individual effect of the sequence for lysine biosynthesis. Expression of the sequence for zein reduction and sequence for lysine biosynthesis preferably does not result in undesirable traits (for example, lower yields, increased susceptibility to pests, diseases, or environmental stress, and decreased seed processing or storage qualities).

The sequence for zein reduction can include any sequence that results in the reduction or decrease of one or more zeins in the maize seed, such as sequence for gene suppression of at least one zein synthesis gene. In one non-limiting embodiment, the sequence for zein reduction includes a sequence for reducing (for example, by gene suppression) seed levels of an alpha-zein, such as a 19-kiloDalton alpha-zein or a 22-kilo-Dalton alpha-zein. In other embodiments, the sequence for zein reduction can include a sequence for reducing seed levels of any one or more of the zein proteins of interest, such as the alpha-, beta-, gamma-, and delta-zeins.

Reduction of zein seed levels can be by any suitable mechanism, including, but not limited to, gene suppression of one or more endogenous zein synthesis genes, or deletion or mutation of one or more endogenous zein synthesis genes, or replacement of one or more endogenous zein synthesis genes with a non-endogenous zein synthesis gene or gene homologue that results in substantially decreased zein seed levels, or transcriptional suppression of zein synthesis gene expression. Gene suppression includes, but is not limited to, any of the well-known methods for suppressing an RNA transcript or production of protein translated from an RNA transcript, including post-transcriptional gene suppression and transcriptional suppression (see, for example, Matzke et al. (2001) *Curr. Opin. Gen. Dev.*, 11:221-227 (2001), and Meister & Tuschl (2004) *Nature*, 431:343-349). Non-limiting methods for effecting gene suppression include gene suppression mediated by inserting a recombinant DNA construct with anti-sense oriented DNA (see, for example, U.S. Pat. Nos. 5,107,065 and 5,759,829; gene suppression by integration of DNA arranged as an inverted repeat resulting from co-insertion of several copies of a transfer DNA into plants by *Agrobacterium*-mediated transformation (see, for example, Redenbaugh et al. in "Safety Assessment of Genetically Engineered Flavr Savr™ Tomato, CRC Press, Inc. (1992), Stam et al. (1997) *Plant J.*, 12:63-82, and Sanders and Hiatt (2005) *Nature Biotechnol.*, 23:287-289); gene suppression by inserting a recombinant DNA construct with sense-oriented DNA (see, for example, U.S. Pat. Nos. 5,283,184 and 5,231,020), gene suppression by transcribing RNA from both a sense and an anti-sense oriented DNA using two separate transcription units (see, for example, U.S. Pat. No. 5,107,065); gene suppression by providing transformation constructs that are capable of generating an RNA that can form double-stranded RNA along at least part of its length (see, for example, published European Patent Application EP 0426195 A1, Sijen et al. (1996) *The Plant Cell*, 8:2277-2294, International Patent Publication Nos. WO98/53083, WO 99/53050, WO 99/49029, and U.S. Patent Application Publication Nos. 2003/0175965, 2003/0036197, 2003/0018993, and 2002/0048814); and gene suppression by transcriptional suppression such as promoter trans suppression (see, for example, Mette et al. (1999) *EMBO J.*, 18:241-148, and Mette et al. (2000) *EMBO J.*, 19:5194-5201). Gene suppression can also be obtained by means of a sequence encoding a DNA or RNA aptamer, as is known in the art (see, for example, Toulme et al. (2004) *FEBS Lett.*, 567: 55-62, Lee et al. (2004) *Nucleic Acids Res.*, 32:95-100, and Nimjee et al. (2005) *Ann. Rev. Med.*, 56:555-583). All of the above-cited patents, patent applications, and publications describing gene suppression are incorporated by reference in their entirety herein.

One recombinant DNA construct useful in introducing sequence for zein reduction into the transgenic plant of the invention is described at length in U.S. patent application Ser. No. 11/057,062, published as U. S. Patent Application Publication No. 2005/0176670A1 and incorporated by reference in its entirety herein. In one non-limiting embodiment, the sequence for zein reduction can include a recombinant DNA construct for suppressing at least one zein gene, which includes, in 5' to 3' order, a promoter element operably linked to an anti-sense-oriented DNA element from the at least one zein gene and a sense-oriented DNA element, wherein the sense-oriented DNA element is shorter than the anti-sense-oriented DNA element, and sense-oriented RNA transcribed by the sense-oriented DNA element is complementary to the 5'-most end of anti-sense-oriented RNA transcribed by the anti-sense-oriented RNA transcribed by the anti-sense-oriented DNA element, wherein the transcribed RNA forms a loop of anti-sense-oriented RNA for suppressing the at least one zein gene. In another embodiment, the sequence for zein reduction can be introduced in the transgenic plant of the invention by providing in cells of the transgenic plant a recombinant DNA construct which is transcribed to RNA that forms a loop of anti-sense-oriented RNA for suppressing at least one zein gene.

The sequence for lysine biosynthesis can include sequence for any gene or genes that confer an increase in lysine levels in the transgenic plant of the invention. Thus, the sequence for lysine biosynthesis can include an exogenous lysine synthesis gene sequence encoding enzymes for synthesis of lysine or its precursors, and/or sequence for gene suppression of a lysine catabolic enzyme endogenous to the transgenic maize plant. Lysine synthesis genes include genes encoding or controlling expression of enzymes for synthesis of lysine or its precursors, such as aspartate kinase (AK) and dihydrodipicolinic acid synthase (DHDPS), and homologues of these genes. Lysine catabolic genes include, but are not limited to, the maize LKR/SDH gene encoding lysine-ketoglutarate reductase (LKR) and saccharopine dehydrogenase (SDH), and its homologues. Useful homologues of these lysine synthesis or catabolic genes may be identified from nucleic acid or protein sequence databases, for example, by using comparison tools known to those in the art, such as, but not limited to, algorithms such as BLAST (Altschul et al. (1997) *Nucleic Acids Res.* 25:3389-3402, which is incorporated by reference herein).

In one preferred embodiment, the sequence for lysine biosynthesis Includes sequence for at least one exogenous lysine synthesis gene, preferably a substantially feedback-insensitive lysine synthesis gene. Substantially feedback-insensitive lysine synthesis genes include, but are not limited to an aspartate kinase that is substantially insensitive to inhibition by lysine such as an *E. coli* AKIII (see U.S. Pat. Nos. 6,459,019 and 5,773,691 and U.S. Patent Application Publication No. 2003/0056242), or a dihydrodipicolinic acid synthase that is substantially insensitive to inhibition by lysine, such as an *E. coli* DHDPS (see U.S. Pat. Nos. 5,288,300, 6,459,019 and 5,773,691 and U.S. Patent Application Publication No. 2003/0056242) or a *Corynebacterium* DHDPS or cordapA (see U.S. Pat. Nos. 6,459,019 and 5,773,691 and U.S. Patent Application Publication No. 2003/0056242); all of these cited patents and patent application are incorporated by reference in their entirety herein. See also U.S. patent application Ser. No. 11/004,221 to Dizigan et al., "High Lysine Maize Compositions and Methods for Detection Thereof," filed 2 Dec. 2004 and now issued as U.S. Pat. No. 7,157,281, which is incorporated by reference in its entirety herein and which discloses a *Corynebacterium* DHDPS or cordapA, which would be a suitable substantially feedback-insensitive lysine synthesis gene.

In another preferred embodiment, the sequence for lysine biosynthesis includes sequence for gene suppression of at least one lysine catabolic enzyme endogenous to said transgenic maize plant, such as a sequence for gene suppression of the LKR or SDH enzymes endogenous to the maize plant. In yet another preferred embodiment, the sequence for lysine biosynthesis includes both sequence for at least one exogenous lysine synthesis gene and sequence for gene suppression of at least one lysine catabolic enzyme endogenous to said transgenic maize plant. In still yet another preferred embodiment, the sequence for lysine biosynthesis includes both sequence encoding a substantially feedback-insensitive lysine synthetic enzyme and a sequence for gene suppression of a lysine catabolic enzyme endogenous to the transgenic maize plant.

The constructs and methods described in U.S. Provisional Patent Application No. 60/638,256, and incorporated by reference in its entirety herein, are particularly useful in introducing sequence for lysine biosynthesis into a transgenic plant of the present invention. In one specific and particularly preferred embodiment, the transgenic plant of the invention has in its genome a sequence for lysine biosynthesis including (a) intron sequence within which is embedded a sequence for gene suppression of at least one lysine catabolic enzyme endogenous to said transgenic maize plant, and, optionally, (b) sequence encoding a substantially feedback-insensitive lysine synthetic enzyme.

The present invention contemplates and claims both maize plants directly regenerated from cells which have been transformed with transgenic DNA including sequence for zein reduction and/or sequence for lysine biosynthesis, as well as progeny of such plants, for example, inbred progeny and hybrid progeny of transformed maize plants. This invention contemplates transgenic maize plants produced by direct transformation with transgenic DNA including sequence for zein reduction and/or sequence for lysine biosynthesis, and transgenic plants made by crossing a plant having transgenic DNA of the invention to a second plant lacking the construct. In one embodiment of the present invention, the transgenic maize plant can include a progeny transgenic maize plant from genetic crossing of a first parent transgenic maize plant having in its genome transgenic DNA including sequence for zein reduction, and a second parent transgenic maize plant having in its genome transgenic DNA including sequence for lysine biosynthesis, wherein the progeny transgenic maize plant from the genetic crossing has in its genome the sequence for zein reduction and the sequence for lysine biosynthesis; seed of the progeny transgenic maize plant has a synergistically increased lysine content when compared to seed from the first and second parent transgenic maize plants.

In a preferred embodiment, seed from the first parent transgenic maize plant having in its genome transgenic DNA including sequence for zein reduction has a higher lysine content than seed from a maize plant with a genotype substantially similar to the first transgenic maize plant but lacking the sequence for zein reduction, and seed from the second parent transgenic maize plant having in its genome transgenic DNA including sequence for lysine biosynthesis also has a higher lysine content than seed from a maize plant with a genotype substantially similar to the first transgenic maize plant but lacking the sequence for lysine biosynthesis. Seed of the progeny transgenic maize plant has a synergistically increased lysine content when compared to seed from the first and second parent transgenic maize plants.

In another embodiment, seeds of transgenic maize plants of the present invention can be harvested from fertile transgenic plants and be used to grow progeny generations of transgenic maize plants of this invention, including hybrid or inbred plant lines that contain in their genome the transgenic DNA including sequence for zein reduction and sequence for lysine biosynthesis and that produce seed with a synergistically increased lysine content.

Method for Providing High-Lysine Maize Seed

The present invention discloses and claims a method for providing maize seed with synergistically increased lysine content, including:
(a) providing a transgenic maize plant having in its genome transgenic DNA including sequence for zein reduction and sequence for lysine biosynthesis,
(b) expressing the transgenic DNA in seed of the transgenic maize plant, the expressing resulting in a synergistically increased lysine content of the seed, and
(c) harvesting the seed with synergistically increased lysine content.

The transgenic maize plant useful in the method of the invention is described above at length under the heading "Transgenic Plants". Preparation of nucleic acid constructs for transformation of plant cells and production of the transgenic plant makes use of techniques well known in the art. See, for example, methodologies disclosed in Sambrook and Russell, "Molecular Cloning: A Laboratory Manual", third edition, Cold Spring Harbor Laboratory Press, 2001, incorporated by reference herein. One versed in the art would be familiar with techniques for transforming plant cells to provide a transgenic plant useful in the method of the invention. See, for example, microprojectile bombardment methods as disclosed in U.S. Pat. Nos. 5,550,318, 5,538,880, 6,160,208, and 6,399,861, and Agrobacterium-mediated transformation methods as described in U.S. Pat. No. 5,591,616, all of which are incorporated herein by reference. Useful techniques for transforming plant cells using site-specific integration include the cre-lox system disclosed in U.S. Pat. No. 4,959, 317 and the FLP-FRT system disclosed in U.S. Pat. No. 5,527,695, both of which are incorporated by reference herein.

Transformation of plant cells to yield transgenic plants useful in the method of this invention is preferably practiced in tissue culture on media and in a controlled environment. Practical transformation methods and materials for making transgenic plants useful in the method of this invention, e.g., various media and recipient target cells, transformation of immature embryos, and subsequent regeneration of fertile transgenic plants, are disclosed in U.S. Pat. Nos. 6,194,636 and 6,232,526, which are incorporated herein by reference.

After delivery of the transgenic DNA to recipient plant cells, transformed cells are generally identified for further culturing and plant regeneration. To improve the ability to identify transformants, one may employ a selectable or screenable marker gene, where the potentially transformed cell population can be assayed by exposing the cells to a selective agent or agents or screened for the desired marker gene trait. Non-limiting examples of screenable markers include a gene expressing a colored or fluorescent protein such as a luciferase or green fluorescent protein (GFP), or a gene expressing a beta-glucuronidase or uidA gene (GUS) for which various chromogenic substrates are known. Non-limiting examples of selectable markers include those conferring resistance to antibiotics such as kanamycin and paromomycin (nptII), hygromycin B (aph IV) and gentamycin (aac3 and aacC4) or resistance to herbicides such as glufosinate (bar or pat) and glyphosate (aroA or EPSPS); particularly useful examples of such selectable markers are illustrated in U.S. Pat. Nos. 5,550,318, 5,633,435, 5,780,708, and 6,118,047, all of which are incorporated by reference herein.

The method of the invention may provide the transgenic maize plant by genetic crossing of a first parent transgenic maize plant having in its genome transgenic DNA including sequence for zein reduction and a second parent transgenic maize plant having in its genome transgenic DNA including sequence for lysine biosynthesis, wherein the genetic crossing results in a progeny transgenic maize plant having in its genome the sequence for zein reduction and the sequence for lysine biosynthesis.

Expression of the transgenic DNA preferably is substantially localized in seed of the transgenic maize plant, for example, substantially localized in the embryo, in the endosperm, or in both the embryo and endosperm, using, for example, promoters described above under the heading "Transgenic Plants". Such expression results in a synergistically increased lysine content of the seed, most preferably a synergistically increased lysine content of the seed at the time of the seed's harvest from the transgenic maize plant. The seed may be harvested and used for any purpose of interest, including, for example, for planting purposes, or for processing into human food products, animal feed products, oils, starches, pharmaceuticals, and various industrial products. Exemplary discussions of the uses of maize can be found, for example, in U.S. Pat. Nos. 6,194,636, 6,207,879, 6,232,526, 6,426,446, 6,429,357, 6,433,252, 6,437,217, and 6,583,338 and PCT Publications WO95/06128 and WO 02/057471, each of which is incorporated by reference in its entirety herein.

EXAMPLES

Example 1

This non-limiting example illustrates a method of the invention for providing maize seed with synergistically increased lysine content, and further illustrates a transgenic maize plant of the invention having in its genome transgenic DNA including sequence for zein reduction and sequence for lysine biosynthesis, whereby expression of the transgenic DNA results in a synergistically increased lysine content of seed of the transgenic maize plant. More specifically, this example describes the genetic crossing of first parent transgenic maize plants (zein reduction lines PQ15 and PQ71, which have in their genome a sequence for zein reduction and show reduction in zein accumulation) and second parent transgenic maize plants (high-lysine line M27908+, which has in its genome a sequence for lysine biosynthesis and shows elevated free lysine caused by expression of an exogenous cordapA gene). These genetic crosses demonstrated that synergistically increased lysine content could be obtained in maize seed from an exemplary transgenic maize plant of the invention.

Transgenic Plants

Zein Reduction Lines

A vector designed to reduce zein was constructed and used for transformation as described in detail by Huang et al. (2004) *J. Agric. Food Chem.*, 52:1958-1964, which is incorporated by reference in its entirety herein. Briefly, a DNA fragment containing nucleotides 965-868 (in the antisense orientation) of the maize 19-kiloDalton alpha-zein gene, Z4 (GenBank accession No. V01472 ), was isolated by PCR. This zein gene coding region fragment was inserted, in the antisense orientation, into an expression cassette that also contained the gamma-zeinA promoter (corresponding to nucleotides 19-1118 of the sequence with GenBank accession No. S78780) to drive high mRNA synthesis, and the 3' untranslated region of the *Agrobacterium tumefaciens* nopaline synthase gene, to provide polyadenylation sequence. These expression cassettes were introduced into immature maize embryos by microprojectile bombardment.

Figure 1B:
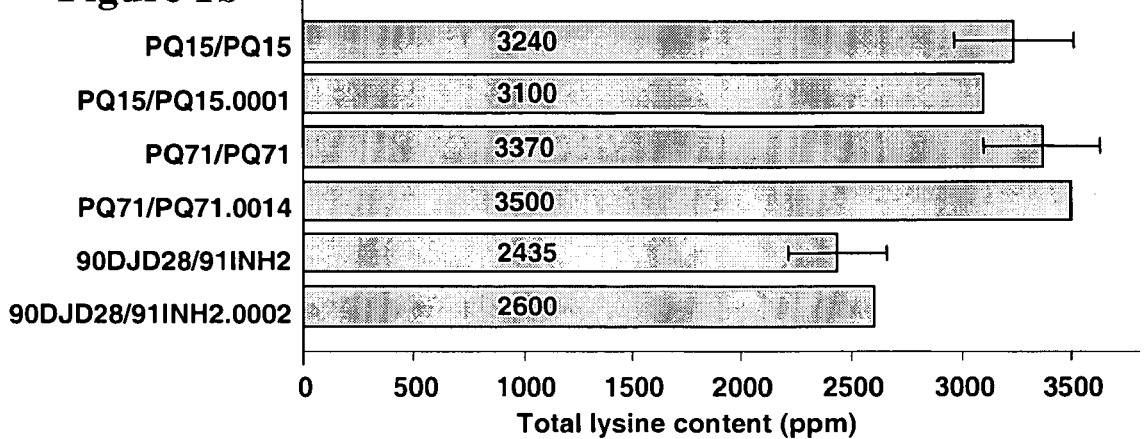
FIG. 1*b* depicts the total lysine content of first parent transgenic maize plants PQ015/PQ15.0001 and PQ071/PQ71.0014 compared to the wild-type maize lines 90DJD28/91INH2 and 90DJD28/91INH2.0002. The error bars on total lysine contents of PQ015/PQ15, PQ071/PQ71, and 90DJD28/91INH2 represent the confidence intervals (alpha =0.05, n =20).

Regenerated R0 transgenic plants were pollinated with wild-type pollen to produce F1 seeds, which were screened for the opaque phenotype and analyzed by SDS-PAGE gels to evaluate the zein profiles. Among the R0 lines found to display a 19-kiloDalton alpha-zein reduction phenotype, two R0 lines, "PQ15" and "PQ71 " (containing 3 copies and 6 copies, respectively, of the transgene) were used in the genetic crossing study. The selected ears for this study, PQ015/PQ15.0001 and PQ071/PQ71.0014, exhibit MALDI-TOF (Matrix-assisted laser desorption ionization time-of-flight) mass spectra that are representative of PQ15 and PQ71 (see FIG. 1a). PQ15 has the most dramatic reduction in 19-kiloDalton alpha-zeins and a slight increase in 22-kiloDalton alpha-zeins, while PQ71 maintains a modest reduction in 19-kiloDalton alpha-zeins, with a large increase in 22-kiloDalton alpha-zeins. Both selected ears also have higher total lysine content than wild-type ears (see FIG. 1b).

High Lysine Lines

Binary plasmids were designed to express cordapA, the lysine-insensitive dihydrodipicolinic acid synthase (DHDPS) from *Corynebacterium glutamicum* (see U.S. Pat. No. 5,773,691, which is incorporated by reference herein). Construction and use of these binary plasmids is described in detail by Huang et al. (2004) *Transgenic Res.*, 13:451-461, which is incorporated by reference in its entirety herein. Briefly, the binary plasmids contained left and right T-DNA border regions flanking an expression cassette that included the maize glb1 promoter, a rice actin intron, the cordapA coding region with a maize DHDPS leader peptide, and the maize glb1 terminator. This expression cassette is designed for embryo-specific expression of cordapA. The binary plasmids also included a selectable marker conferring glyphosate resistance, epsps-cp4 (5-enolpyruvylshikimate-3-phosphate synthase from *Agrobacterium tumefaciens* strain CP4). Conventionally, the selectable marker (epsps-cp4) would be typically placed adjacent to the gene of interest (cordapA), allowing both the cordapA expression cassette and the epsps-cp4 selectable marker to be co-integrated when transformed into a plant cell, thus enhancing recovery of plants containing the cordapA transgene by selection under glyphosate. Instead, alternative binary vectors were constructed (see FIG. 3 in Huang et al. (2004) *Transgenic Res.*, 13:451-461), where the epsps-cp4 marker was either (1) placed in would normally be considered the "backbone" of the vector, rather than within the T-DNA region and adjacent to the gene of interest, cordapA (vectors pMON65178 and pMON65179), or (2) located between a second set of left and right T-DNA border regions (vector pMON65180).

R0 plants that were identified as positive for cordapA were assayed by Southern blot to determine the frequency of plants containing cordapA unlinked to the selectable marker, epsps-cp4. The vector that produced the highest percentage (35.6%) of unlinked events was pMON65178, which contained epsps-cp4 in the backbone of the vector and adjacent to the cordapA expression cassette. R1 seedlings derived from R0 plants with unlinked insertions were tested for the segregation of epsps-cp4 and cordapA by PCR.

Marker-free segregants that were cordapA-positive and epsps-cp4-negative were identified from 93% of unlinked events transformed by pMON65178. pMON65178 included right border and left border sequences flanking an expression cassette containing the maize glb1 promoter, a rice actin intron, the *cordapA* coding region (nucleotides 3 through 903 of the sequence disclosed as SEQ ID NO: 6 in U.S. Pat. No. 6,459,019, which is incorporated by reference herein) with a maize DHDPS leader peptide, and the maize glb1 terminator, with the epsps-cp4 marker placed in the plasmid "backbone" and adjacent to the T-DNA region. Other functional cordapA genes could be used, such as, but not limited to, the full length 917 base pair sequence disclosed as SEQ ID NO: 6 in U.S. Pat. No. 6,459,019, or the *Corynebacterium* dapA gene sequence published by Bonnassie et al. (1990) *Nucleic Acids Res.*, 18:6421, both of which are incorporated herein by reference, or lysine-insensitive homologues of these genes which may be identified by sequence comparison tools known in the art, for example, a BLAST algorithm. One of the marker-free cordapA transgenic lines generated by this approach was M27908. Seeds derived from this event have an average of 2505 ppm free lysine content compared to seeds from its wild-type segregant, which contain an average of 71 ppm free lysine.

Figure 2A:
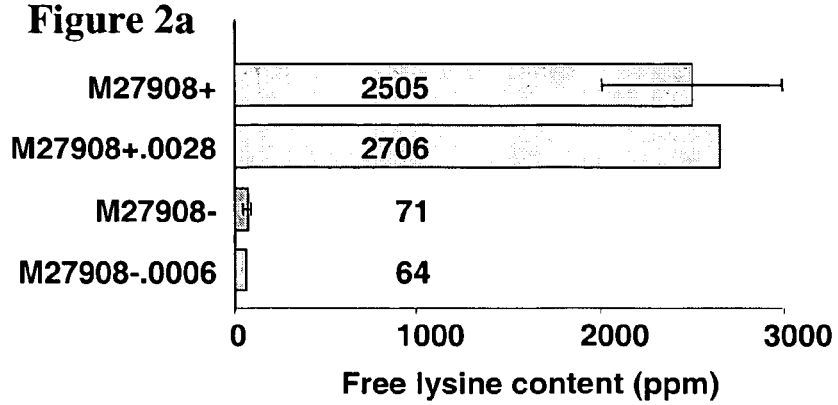
FIG. 2a depicts results of free lysine analyses. The error bars are the standard deviations of sibling ears.
Figure 2B:
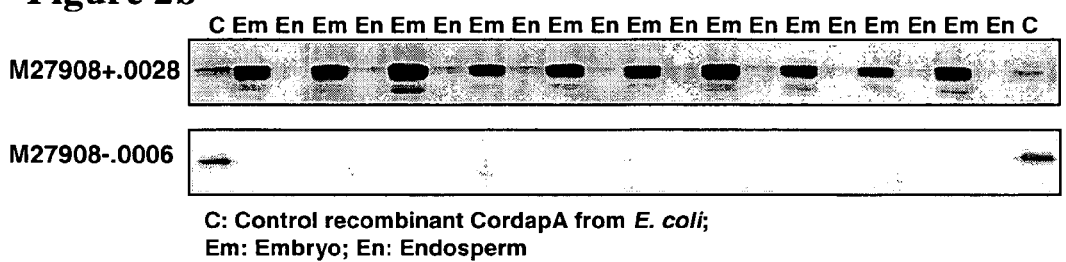
FIG. 2b depicts results of cordapA Western analysis of individual mature kernels. An embryo-specific expression of CordapA was observed, and the homozygosity of the ear, M27908+.0028 was confirmed.
Figure 2C:
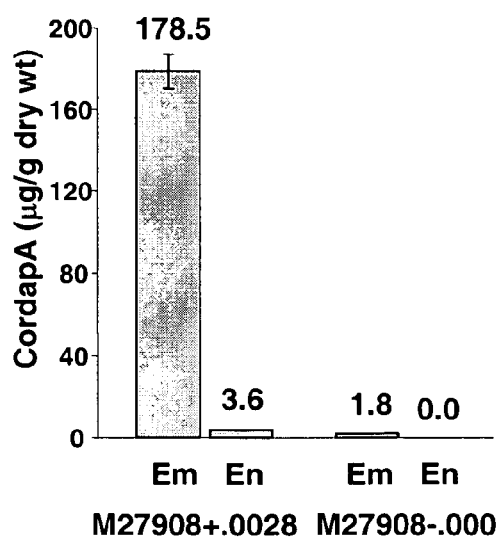
FIG. 2c depicts CordapA ELISA results, which further confirmed the embryo-specific accumulation of CordapA. The error bars are the standard deviations of experimental replicates.
Figure 2D:
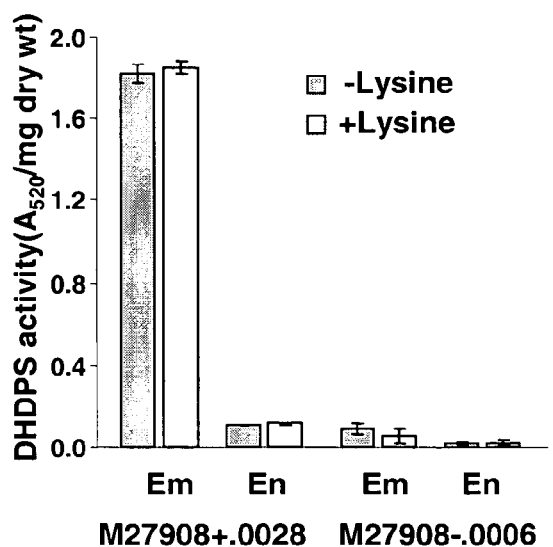
FIG. 2d depicts results of a lysine insensitive DHDPS activity assay. The concentration of lysine used in the DHDPS activity assay was 1 millimolar.

Transgenic lines M27908+.0028 and M27908−.0006 were used as the cordapA and wild-type control in the crossing experiment, which contain free lysine levels of 2706 and 64 ppm, respectively (FIG. 2*a*). The embryo-specific expression of cordapA was confirmed by Western blots and ELISA assays (FIG. 2*b* and FIG. 2*c*). Transgenic M27908+.0028 embryos also displayed elevated DHDPS activity, even in the presence of lysine (FIG. 2*d*).

Genetic Crossing of Reduced-Zein and High-Lysine Maize Lines

Genetic crossing was carried out with first parent transgenic maize plants (zein reduction lines PQ15 and PQ71, which have in their genome a sequence for zein reduction) and second parent transgenic maize plants (high-lysine line M27908+, which has in its genome a sequence for lysine biosynthesis). The zein reduction lines, PQ15, PQ71 and their wild-type control, 90DJD28/91INH2, were used as females and pollinated with the high-lysine line, M27908+, and its wild-type control, M27908−, in the field. Table 1 lists the resulting six different F1 genotypes, their designations, and the numbers of ears harvested and analyzed. All the transgenic kernels that resulted from the crosses of homologous transgenic parents were hemizygous. More than twenty F1 ears from two separate plots from each cross were harvested and analyzed; only ears with about 150 to about 400 kernels per ear were selected for analysis.

TABLE 1

| Ear designation | Female parent | Male parent | Plot 1 | Plot 2 | Total |
|---|---|---|---|---|---|
| PQ15/CordapA | PQ15/PQ15.0001 | M27908 + .0028 | 12 | 14 | 26 |
| PQ15 | PQ15/PQ15.0001 | M27908 − .0006 | 10 | 12 | 22 |
| PQ71/CordapA | PQ71/PQ71.0014 | M27908 + .0028 | 10 | 13 | 23 |
| PQ71 | PQ71/PQ71.0014 | M27908 − .0006 | 12 | 11 | 23 |
| CordapA | 90DJD28/91INH2.0002 | M27908 + .0028 | 17 | 11 | 28 |
| Control | 90DJD28/91INH2.0002 | M27908 − .0006 | 13 | 15 | 28 |

Analyses:

Kernel Dissection

To facilitate the kernel dissection, mature dry kernels were submerged in water and stored at 4 degrees Celsius overnight. Fifty kernels per ear were dissected and lyophilized to remove water. After recording the dry weights of the separated embryo and endosperm, the samples were ground to powder. Water imbibition was not found to significantly affect the following amino acid and proximate analyses.

CordapA Extraction and Activity Assay

Dried embryo and endosperm powders were extracted with a 1:3 ratio of tissue to hexane several times at 50 to 55 degrees Celsius for 3 to 10 minutes. After hexane extraction, the powder was lyophilized and stored at 4 to 6 degrees Celsius. CordapA and native DHDPS were extracted with 20 millimolar Tris-HCl, pH 8.0, 100 millimolar KCl, and 10 millimolar sodium pyruvate. A 1:5 ratio of tissue to CordapA extraction buffer was used with shaking for 1 hour at 4 degrees Celsius. The extract was microcentrifuged for 5 minutes at 14,000×g. For the assay (adopted from Frisch et al. (1991) *Plant Physiol.*, 96:444-452, which is incorporated by reference), the extract supernatant was further diluted six-fold in extraction buffer. Twenty microliters of the diluted extract was added to the wells of a microplate. To begin the reaction, 180 microliters of reaction buffer was added which contained 200 millimolar Tris-HCl, pH 8.0, 16 millimolar sodium pyruvate, 1 millimolar ASA (L-aspartic acid-beta-semialdehyde hydrate trifluoroacetate) and plus or minus 1 millimolar lysine monohydrochloride. The ASA was obtained from Gateway Chemical Technology, St. Louis and dissolved in 4 normal HCl to yield a 140 millimolar stock solution. Before use, the 140 millimolar ASA stock was diluted to 14 millimolar by adding 100 microliters of the 140 millimolar ASA stock to 100 microliters of 1 molar Tris-HCl, pH 8.0 and 800 microliters of 1 normal NaOH. The reaction was allowed to proceed for 1 hour at 37 degrees Celsius and then stopped by addition of 100 microliters of endpoint colorimetric reagent. This reagent was made by dissolving 20 milligrams ortho-aminobenzaldehyde in 0.3 milliliters of ethanol, which was then added to 11.7 milliliters of 0.22 molar citrate-0.55 molar phosphate buffer pH 5.5. Color was allowed to develop for 10 minutes at room temperature and the absorbance read at 520 nanometers with a SpectraMax Plus microplate reader (Molecular Devices, Sunnyvale, Calif.).

CordapA Western Blot

Twenty milligrams of ground endosperm or embryo were incubated in 200 microliters SDS-borate buffer (60 millimolar $Na_2B_4O_7 \cdot 10 H_2O$ pH 10, 4% SDS, 1.5 milligrams/milliliter dithiothreitol) at 65 degrees Celsius for 1.5 hours. Samples were spun at 14000 rpm for 5 minutes and 60 microliters supernatant transferred to a 96-well PCR plate containing 30 microliters 3X SDS-PAGE loading buffer (Bio-Rad, Hercules, Calif.). The sample plate was heated at 98 degrees Celsius for 10 minutes then cooled and stored at 4 degrees Celsius until loading. Twenty-four well pre-cast SDS-PAGE (4-20%) gels (Bio-Rad) were loaded with 13 microliters of sample each along with purified recombinant CordapA and prestained MW standard (Bio-Rad) for reference. Gels were run at constant voltage (90 volts) until the dye front reached the bottom of the gel; the gels were then transferred to PVDF membrane (Bio-Rad). The goat anti-CordapA antibody was produced by immunizing goats against *E. coli*-expressed recombinant CordapA. The Immun-Blot Assay Kit containing rabbit anti-goat IgG alkaline phosphatase conjugate (Bio-Rad) was used for detection following the manufacturer's protocols.

CordapA ELISA

A hundred milligrams of dry dissected embryo or endosperm powder was analyzed. After adding 2.5 milliliters of cold extraction buffer (50 millimolar $Na_2B_4O_7 \cdot 10 H_2O$, 0.75 molar KCl, 0.2% v/v Tween20, 36 millimolar NaOH, and 10 millimolar L-ascorbic acid) the sample was vortexed vigorously at 4 degrees Celsius for 30 minute. The extracts were filtered, and aliquots of samples were stored at −20 degrees Celsius. A series of dilutions (1/10, 1/100, 1/1000, 1/5000) was made and used for the analysis. A hundred microliters of diluted primary antibody (2.4 micrograms/milliliter) was added to each well of a Nunc Immuno plate (VWR, West Chester, Pa.) and incubated at 4 degrees Celsius. The plates were washed 3 times with PBST (137 millimolar NaCl, 8.1 millimolar $Na_2HPO_4 \cdot 7H_2O$, 1.5 millimolar $KH_2PO_4$, 2.7 millimolar KCl and 0.05% v/v Tween20) and incubated for 1 hour at 37 degrees Celsius with 100 microliters of TBA (100 millimolar Tris, 100 millimolar $Na_2B_4O_7 \cdot 10H_2O$ pH 7.8, 5 M $MgCl_2$, 0.05% v/v Tween20, and 0.2% (v/v) L-ascorbic acid) with 0.1% dry milk to block against non-specific protein adsorption, then washed again 3 times with PBST. Serial dilutions of CordapA protein in TBA were made (1.6, 0.8, 0.4, 0.2, 0.1, 0.05 nanograms/milliliter) as standards. One hundred microliters of each standards and sample dilutions were loaded in triplicate onto the plates and incubated for 1 hour at 37 degrees Celsius. After washing 3 times with PBST, 100 microliters of 1:10000 dilution in TBA of Biotin conjugated goat anti-CordapA primary antibody was added to each well and plates incubated for 1 hour at 37 degrees Celsius. After washing 3 times with PBST, a second incubation with a 1:10000 dilution of Neutravidin-HRP conjugated mouse anti goat IgG (KPL Inc., Gaithersburg, Md.) was added. After washing 3 times with PBST, a ten-minute incubation with 100 microliters of TMB substrate/$H_2O_2$ (1:1) (VWR) was followed, and the reaction was stopped by addition of 100 microliters of 6 molar $H_3PO_4$. Absorbance was read at 450 nanometers using a SpectraMax Plus microplate reader (Molecular Devices).

Matrix-Assisted Laser Desorption Ionization Time-of-Flight Mass Spectrometry

Individual kernels were powdered and extracted with an ethanol buffer (70% ethanol, 25 millimolar ammonium hydroxide, and 10 millimolar dithiothreitol) at a ratio of 40 milligrams kernel powder to 1 milliliter buffer. Samples were incubated for 1 hour in a 60 degrees Celsius water bath, with periodic shaking and centrifuged for 15 minutes at 1000 rpm. One microliter of each sample was then mixed with 8 microliters of matrix (10.4 milligram/milliliter of 2-(4'-hydroxyazobenzene)-benzoic acid (HABA) in 70% acetonitrile with 0.3% trifluoroacetic acid) using Applied Biosystems (Framingham, Mass.) SymBiot™ I robot. From this mixture, 0.6 microliters was deposited on a 384-position MALDI target plate (Applied Biosystems). Carbonic anhydrase (Sigma, St. Louis, Mo.) was included in the matrix mixture (1 millimolar) as an internal standard to normalize the spectra. Matrix-assisted laser desorption ionization time-of-flight mass spectrometry (MALDI-TOF MS) analysis was performed using an Applied Biosystems Voyager-DETM PRO Biospectrometry™ Workstation with a 337 nanometer nitrogen laser. A detailed description of the MALDI-TOF MS method for analyzing zein proteins has been published by Adams et al. (2004) *J. Agric. Food Chem.*, 52:1842-1849, which is incorporated by reference herein.

Amino Acid Analysis

Ground meal samples (50 milligrams) from pools of whole kernels or dissected embryo and endosperm were extracted with 5% TCA at 4 degrees Celsius overnight. Extracts were filtered, diluted if necessary, and analyzed for free amino acids by the OPA method, which uses ortho-phthaldialdehyde to derivatize samples before injection onto a C18, reverse phase HPLC column (Zorbax Eclipse-AAA, XDB C-18, 4.6 millimeters×75 millimeters, 3.5 micrometers, Agilent Technologies, Palo Alto, Calif.) followed by a guard column (Zorbax Eclipse-AAA, 4.6 millimeters×12.5 millimeters, 5 micrometers, Agilent Technologies, Palo Alto, Calif.). We used an Agilent HPLC (model 1100) equipped with a fluorescence detector. For total amino acid analysis, protein hydrolysis was performed prior to OPA derivation. Samples (60 milligrams) were hydrolyzed with 10 milliliters of 6 normal HCl and 10 microliters of phenol at 110 degrees Celsius for 24 hours under argon. Aliquots were dried down and redissolved in 0.1 normal HCl for OPA derivation and subsequent HPLC analysis. Lysine measurements were repeated by LC-MS/MS. The lysine metabolites, alpha-aminoadipic delta-semialdehyde ("AAA") and saccharopine ("Sac") were also measured.

Composition Analysis

The proximate contents of bulked kernels from each ear in Table 2 were determined by near-infrared transmission (NIT) analysis (as described by Dyer and Feng (1997) *Feedstuffs*, 69:16-25, which is incorporated by reference) using an Infratec 1221 Grain Analyzer (Foss, Eden Prairie, Minn.). The total protein content of dissected embryo and endosperm presented in Table 2 was determined with a FP-528 Protein/Nitrogen Determinator (LECO, St. Joseph, Mich.) following AOCS (American Oil Chemical Society) official method Ba 4f-00.

LKR/SDH Extraction and Activity Assay

This extract preparation procedure was adapted and modified from Goncalves-Butruile et al (1996) *Plant Physiol.*, 110:765-771, Gaziola et al. (1999) *J. Agric. Food Chem.*, 47:1268-1275, and Kemper et al. (1998) *Eur. J. Biochem.*, 253:720- 729, all of which are incorporated by reference herein. Fresh frozen ground corn kernels of the germplasms of interest (300-600 milligrams) were placed into 2 milliliter tube with Lysing matrix E (Q-Biogen, Irvine, Calif.) premixed with 150 microliters (dry volume) of polyvinylpyrrolidone. A volume of 625 microliters of extract buffer (50 millimolar $KH_2PO_4$:$K_2HPO_4$ pH 7.4, 125 millimolar NaCl, 2.0 millimolar $MgCl_2$, 1.0 millimolar EDTA, 250 micromolar $CaCl_2$, 10% Glycerol, CHAPS 0.1%, 8 millimolar NaF, 4 millimolar DTT, and one complete protease tablet (Roche, Indianapolis, Ind.) was added on top of ground kernels and matrix. Samples were homogenized using a Fast Prep machine (Q-Biogen). Homogenates were placed on ice, with occasional mixing/agitation, for 15-20 minutes before centrifugation at 14,000×g for 15 minutes. The supernatant (550 to 625 microliters) was removed from packed debris and placed in a separate tube. This sample was fractionated by PEG precipitation (PEG 8000 50% w/v in water) at 7.5 and 15%. The 15% pellet (which contained the LKR and SDH activity) was resuspended in fresh extract buffer (150-300 microliters) and LKR and SDH activity analyzed. All procedures were performed at 4 degrees Celsius or on ice (except homogenization at room temperature).

LKR and SDH activity were analyzed spectrophotometrically (see, for example, protocols described by Goncalves-Butruile et al. (1996)) for 10 to 20 minutes by observing the rate of oxidation of NADPH or the rate of reduction of $NAD^+$ respectively, at 340 nanometers and 30 degrees Celsius in a Tecan Safire2 (Tecan US, Research Triangle Park, N.C.). The reaction sample volume was 200 microliters for both assays. The LKR assays contained 25 millimolar lysine, 13.3 millimolar alpha-ketoglutaric acid, 325 micromolar NADPH, and 10 to 30 microliters of extract in 100 millimolar K-H$_2$PO$_4$: K$_2$HPO$_4$ pH 7.0, 1 millimolar EDTA, and 10 millimolar MgCl$_2$. Negative controls contained everything except alpha-ketoglutaric acid. The SDH assays contained 2.15 millimolar L-saccharopine, 2.5 millimolar NAD$^+$ and 10 to 30 microliters of extract in 100 millimolar KH$_2$PO$_4$:K$_2$HPO$_4$ pH 8.4, 20millimolar TAPS, and 1 millimolar EDTA. Negative controls contained everything except L-saccharopine. Specific activities are reported in nanomoles NADPH oxidized or NAD$^+$ reduced per minute per milligram of protein. Protein concentrations were determined by using the Bradford reagent from Bio-Rad.

Results

Mass Spectral Zein Analysis

Figure 3:
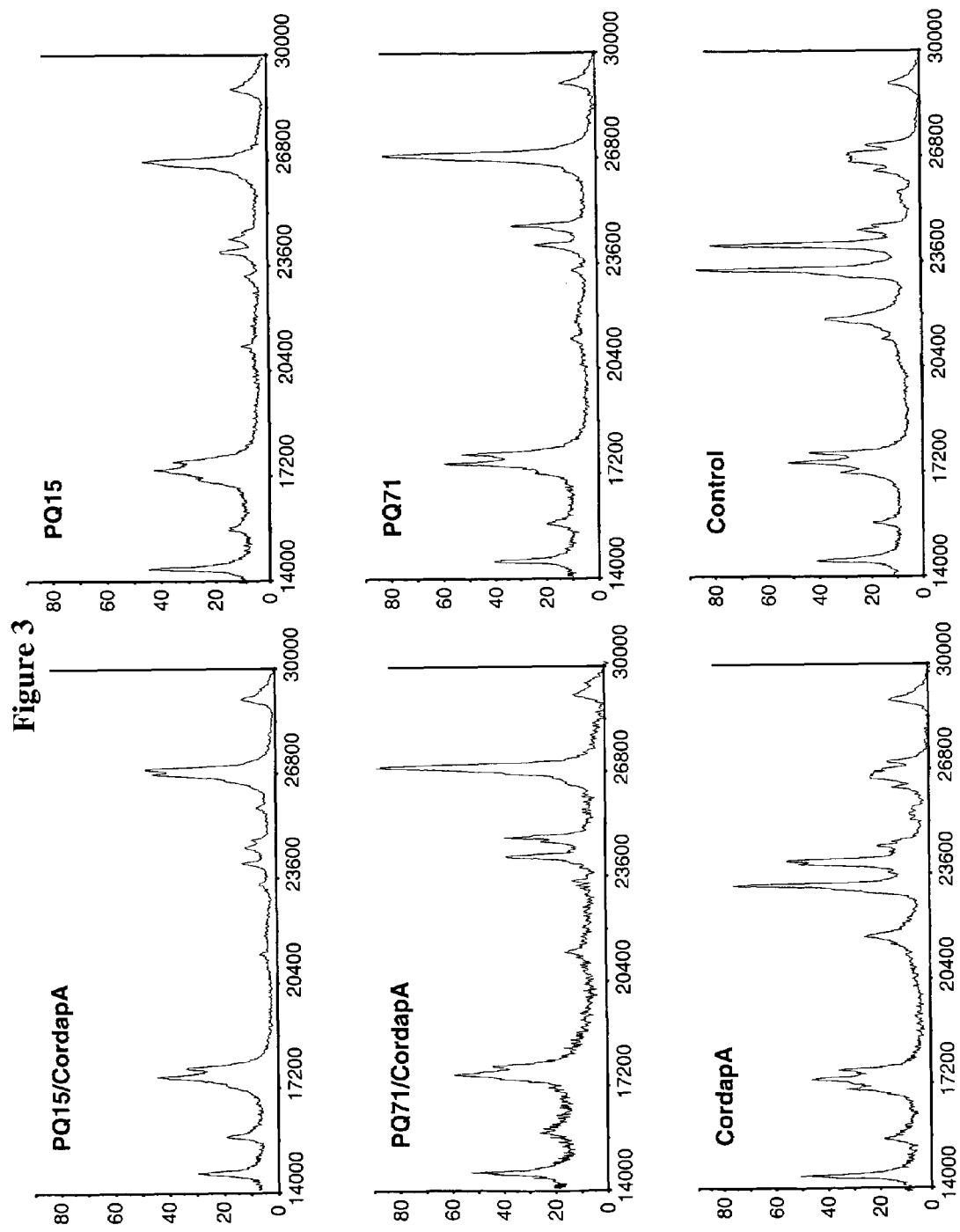
FIG. 3 depicts representative matrix-assisted laser desorption ionization time-of-flight mass spectra analyses of seed from F1 progeny transgenic maize plants PQ15/CordapA and PQ71/CordapA, showing similar zein profiles to the respective parent transgenic maize plants PQ015/PQ15.0001 ("PQ15") and PQ071/PQ71.0014 ("PQ71"), which have in their genome a sequence for zein reduction. See Example 1. Mass spectra of seed from CordapA and Control are comparable to 90DJD28/91INH2.0002. X-axis is shown as m/z (mass to charge) ratios. Y-axis is shown as percent intensity.
Figure 4:
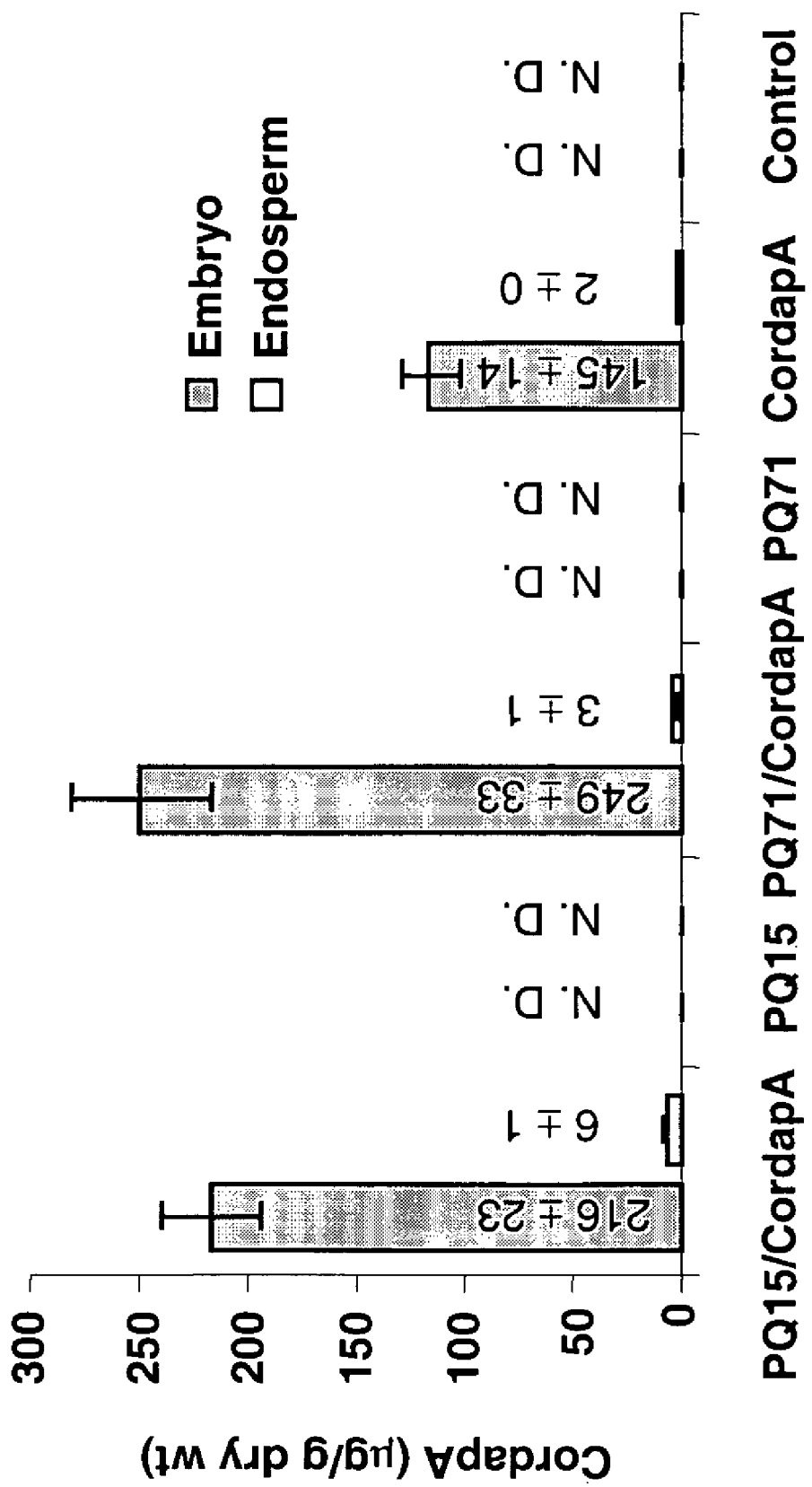
FIG. 4 depicts CordapA ELISA results for dissected seed from F1 progeny transgenic maize plants, PQ15/CordapA and PQ71/CordapA, confirming embryo-specific expression of the sequence for lysine biosynthesis, cordapA. See Example 1. In PQ15/CordapA and PQ71/CordapA, the expression of CordapA is higher than in the control F1, CordapA, which lacks the sequence for zein reduction. The error bars represent the confidence intervals (alpha=0.05, n>20). N. D., not detected.
Figure 5:
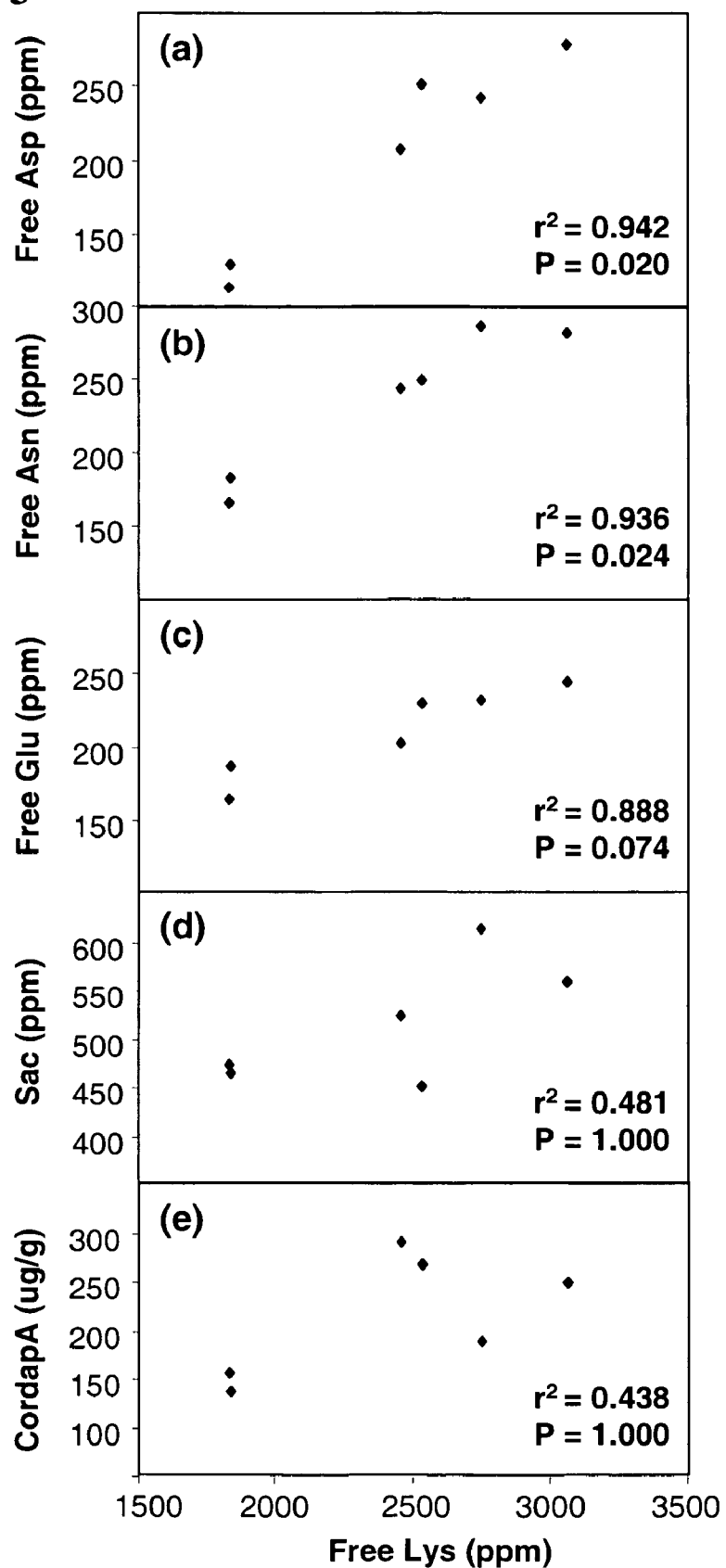
FIG. 5 depicts Pearson's correlations between free lysine and other components of the lysine biosynthesis pathway in the F1 progeny transgenic maize plants, PQ15/CordapA and PQ71/CordapA and the parent transgenic plant CordapA. See Example 1, Table 3.

Since the parents of the F1 crosses were both homozygous for their respective transgenes, the F1 kernels were uniformly hemizygous for both transgenic loci. To ensure the expression of transgenic loci in the F1 generation, the zein composition of individual kernels was examined by MALDI-TOF mass spectral analysis. The representative spectra for F1 kernels from each cross were found to be similar to the zein reduction lines from which they originated (FIG. 3). In addition, all CordapA containing F1s retained the embryo-specific expression of CordapA (FIG. 4). While the presence of the CordapA transgene did not change the zein profiles in these F1s, its expression is noticeably higher in the zein reduction F1s.

Whole Kernel Proximate Analyses

Table 2 gives the results of the near-infrared transmission (NIT) proximate analysis and size of bulked kernels produced by transgenic and wild-type ears. The data presented are means plus or minus confidence intervals (alpha=0.05). The sizes were measured in 100-kernel weights in grams. Total protein weights are presented as total protein weights of 100 kernels in grams, which were calculated by multiplying protein content by 100-kernel size. The relatively small differences observed between PQ15/CordapA and PQ15, PQ71/CordapA and PQ71, and CordapA and Control, suggested that CordapA did not contribute to any significant change in kernel proximate composition. On the other hand, the impact of zein reduction in the kernel proximate composition was detectable. The PQ15/CordapA and PQ15 materials that appeared to have the most dramatic reduction in zein proteins, also appeared to have lower protein content, lower seed density and smaller seed size. When the protein weight per 100 kernels was calculated, PQ15/CordapA and PQ15 had an average of 25% reduction compared to their non-zein reduction counterparts, CordapA and Control. The slightly higher protein contents of PQ71/CordapA and PQ71 materials were offset by their slightly smaller sizes, and their protein weights per 100 kernels were indistinguishable from those of CordapA and Control. The oil content of the PQ15/CordapA and PQ15 seeds were noticeably higher than others (consistent with observations for the previous generation), although it was unclear whether this was caused by the zein reduction since the other zein reduction line, PQ71, had normal oil content.

TABLE 2

| | % ± CI | | | | | |
|---|---|---|---|---|---|---|
| | PQ15/CordapA | PQ15 | PQ71/CordapA | PQ71 | CordapA | Control |
| Oil | 5.7 ± 0.2 | 5.4 ± 0.3 | 4.4 ± 0.1 | 4.5 ± 0.2 | 4.6 ± 0.1 | 4.5 ± 0.1 |
| Protein | 9.2 ± 0.5 | 9.4 ± 0.4 | 10.6 ± 0.8 | 11.6 ± 0.7 | 9.5 ± 0.5 | 10.1 ± 0.6 |
| Starch | 69.0 ± 0.4 | 69.0 ± 0.4 | 69.3 ± 0.6 | 69.5 ± 0.5 | 70.7 ± 0.4 | 70.3 ± 0.6 |
| Moisture | 10.7 ± 0.4 | 10.5 ± 0.2 | 10.2 ± 0.2 | 10.7 ± 0.1 | 11.0 ± 0.1 | 11.1 ± 0.2 |
| Density | 1.22 ± 0.01 | 1.23 ± 0.01 | 1.29 ± 0.01 | 1.31 ± 0.01 | 1.30 ± 0.00 | 1.31 ± 0.01 |
| Size | 25.11 ± 1.04 | 23.97 ± 1.10 | 26.81 ± 1.10 | 27.71 ± 1.04 | 29.49 ± 1.37 | 30.68 ± 1.41 |
| Protein weight | 2.32 ± 0.19 | 2.25 ± 0.15 | 2.85 ± 0.24 | 3.22 ± 0.26 | 2.79 ± 0.19 | 3.13 ± 0.28 |

Whole Kernel Free Amino Acid and Lysine Metabolite Analysis

The whole kernel free amino acid analysis results are given in Table 3, with the data in parts per million (ppm) and presented as averages of two plots plus or minus a standard deviation. The levels of lysine and its metabolites, alpha-aminoadipic delta-semialdehyde (AAA) and saccharopine (Sac), as measured by LC-MS/MS, are also given.

TABLE 3

| | Ave ± SD | | | | | |
|---|---|---|---|---|---|---|
| | PQ15/CordapA | PQ15 | PQ71/CordapA | PQ71 | CordapA | Control |
| Ala | 94 ± 11 | 140 ± 25 | 94 ± 11 | 129 ± 29 | 88 ± 11 | 108 ± 9 |
| Arg | 88 ± 1 | 80 ± 14 | 85 ± 4 | 79 ± 21 | 69 ± 8 | 47 ± 1 |
| Asn | 284 ± 3 | 515 ± 11 | 247 ± 4 | 424 ± 122 | 174 ± 13 | 194 ± 9 |
| Asp | 261 ± 26 | 365 ± 66 | 229 ± 31 | 299 ± 39 | 121 ± 11 | 125 ± 5 |
| Glu | 239 ± 9 | 412 ± 85 | 217 ± 19 | 323 ± 67 | 176 ± 16 | 227 ± 11 |
| Gln | 88 ± 10 | 123 ± 14 | 77 ± 5 | 126 ± 42 | 65 ± 21 | 74 ± 2 |
| Gly | 51 ± 1 | 58 ± 5 | 52 ± 1 | 59 ± 4 | 51 ± 2 | 54 ± 2 |
| His | 41 ± 1 | 41 ± 3 | 38 ± 1 | 38 ± 4 | 37 ± 2 | 30 ± 0 |
| Ile | 15 ± 2 | 19 ± 3 | 13 ± 0 | 16 ± 1 | 14 ± 1 | 17 ± 1 |
| Leu | 27 ± 2 | 31 ± 5 | 24 ± 2 | 26 ± 5 | 22 ± 1 | 19 ± 1 |
| Lys | 2908 ± 218 | 64 ± 6 | 2498 ± 52 | 67 ± 16 | 1838 ± 1 | 43 ± 4 |

TABLE 3-continued

| | Ave ± SD | | | | | |
|---|---|---|---|---|---|---|
| | PQ15/CordapA | PQ15 | PQ71/CordapA | PQ71 | CordapA | Control |
| Met | 15 ± 2 | 17 ± 4 | 15 ± 1 | 17 ± 1 | 14 ± 1 | 13 ± 1 |
| Phe | 20 ± 1 | 27 ± 2 | 18 ± 0 | 22 ± 2 | 18 ± 1 | 18 ± 1 |
| Ser | 80 ± 7 | 125 ± 19 | 73 ± 8 | 107 ± 15 | 73 ± 6 | 90 ± 0 |
| Thr | 22 ± 4 | 46 ± 11 | 21 ± 5 | 38 ± 8 | 17 ± 2 | 21 ± 0 |
| Trp | 19 ± 1 | 17 ± 1 | 15 ± 0 | 15 ± 1 | 16 ± 1 | 14 ± 1 |
| Tyr | 55 ± 4 | 66 ± 1 | 74 ± 24 | 74 ± 4 | 50 ± 3 | 39 ± 1 |
| Val | 33 ± 2 | 45 ± 9 | 28 ± 1 | 38 ± 7 | 27 ± 1 | 30 ± 0 |
| Total | 4335 ± 300 | 2187 ± 281 | 3814 ± 166 | 1892 ± 390 | 2965 ± 100 | 1158 ± 13 |
| AAA* | 80 ± 1 | 13 ± 0 | 59 ± 5 | 9 ± 2 | 81 ± 3 | 9 ± 1 |
| Sac* | 588 ± 37 | 25 ± 6 | 488 ± 52 | 13 ± 4 | 459 ± 6 | 17 ± 1 |
| Lys* | 3148 ± 144 | 55 ± 1 | 2704 ± 45 | 64 ± 20 | 1918 ± 14 | 31 ± 5 |

*measured by LC-MS/MS

The whole kernel free lysine content of all of the F1 materials containing the CordapA transgene was very high, and was accompanied by increases in the lysine metabolites, alpha-aminoadipic delta-semialdehyde and saccharopine. Unexpectedly, zein reduction appeared to synergistically increase the accumulation of free lysine caused by the expression of CordapA (2908 and 2498 ppm in PQ15/CordapA and PQ71/CordapA vs. 1838 ppm in CordapA). Other than lysine, among the amino acids examined, asparagine, aspartate, glutamate and glutamine had significant increases in the PQ15 and PQ71 lines. However, when combined with CordapA, as in PQ15/CordapA and PQ71/CordapA, the levels of these amino acids resembled those in Control material.

Whole Kernel Total Amino Acid Analysis

The whole kernel total amino acid analysis results are given in Table 4, with the data in parts per million (ppm) and presented as averages of two plots plus or minus a standard deviation. Asparagine and aspartate are combined ("Asx"); glutamine and glutamate are combined ("Glx").

As shown in Table 4, the most significant differences observed among the amino acids quantified in the whole F1 kernels analyzed were in the lysine contents. PQ15 and PQ71 were found to have elevated total lysine levels when compared to the Control. In addition, after the subtraction of their free lysine contents, the total lysine contents of PQ15/CordapA, PQ71/CordapA and CordapA were similar to those in PQ15, PQ71 and Control respectively (see Table 3).

Dissected Embryo and Endosperm-Free Amino Acid and Lysine Metabolite Analysis

The free amino acid analysis results for the dissected embryos and endosperms are given in Table 5, with the data in parts per million (ppm) and presented as averages of two plots plus or minus a standard deviation. Samples were pooled by equal amount of ground mills from each ear harvested from a plot. The levels of lysine and its metabolites, alpha-aminoadipic delta-semialdehyde (AAA) and saccharopine (Sac), as measured by LC-MS/MS, are also given.

TABLE 4

| | Ave ± SD | | | | | |
|---|---|---|---|---|---|---|
| | PQ15/CordapA | PQ15 | PQ71/CordapA | PQ71 | CordapA | Control |
| Ala | 6085 ± 120 | 6270 ± 0 | 6915 ± 233 | 8395 ± 516 | 6330 ± 212 | 6885 ± 233 |
| Arg | 4525 ± 35 | 4620 ± 113 | 4700 ± 269 | 5405 ± 233 | 4140 ± 198 | 4470 ± 85 |
| Asx | 5435 ± 163 | 6005 ± 64 | 5875 ± 106 | 7500 ± 283 | 5030 ± 170 | 5100 ± 28 |
| Glx | 15590 ± 382 | 16420 ± 127 | 18440 ± 665 | 23060 ± 1499 | 16825 ± 544 | 17825 ± 502 |
| Gly | 3475 ± 35 | 3495 ± 120 | 3415 ± 163 | 3985 ± 134 | 3210 ± 85 | 3365 ± 35 |
| His | 1625 ± 49 | 1725 ± 78 | 1770 ± 354 | 2210 ± 212 | 1955 ± 64 | 1530 ± 198 |
| Ile | 2925 ± 78 | 2840 ± 113 | 3125 ± 49 | 3895 ± 191 | 2965 ± 92 | 3125 ± 177 |
| Leu | 8960 ± 156 | 9125 ± 92 | 10700 ± 297 | 13045 ± 884 | 10540 ± 325 | 11570 ± 495 |
| Lys | 6160 ± 354 | 2930 ± 127 | 5475 ± 375 | 3320 ± 269 | 4290 ± 269 | 2575 ± 21 |
| Phe | 3005 ± 35 | 3045 ± 7 | 3340 ± 57 | 4075 ± 205 | 3435 ± 92 | 3705 ± 120 |
| Ser | 3825 ± 21 | 4110 ± 28 | 4320 ± 283 | 5245 ± 290 | 4065 ± 163 | 4400 ± 71 |
| Thr | 3050 ± 28 | 3155 ± 7 | 3280 ± 170 | 4105 ± 120 | 3075 ± 92 | 3240 ± 99 |
| Tyr | 3525 ± 21 | 3675 ± 7 | 3970 ± 255 | 4915 ± 262 | 3745 ± 120 | 4010 ± 99 |
| Val | 4220 ± 99 | 4140 ± 127 | 4465 ± 49 | 5530 ± 240 | 3850 ± 113 | 4055 ± 177 |
| Total | 72405 ± 1478 | 71555 ± 322 | 79790 ± 2206 | 94685 ± 4914 | 72915 ± 2539 | 75855 ± 1718 |
| Lys % | 8.5 ± 0.3% | 4.1 ± 0.2% | 6.9 ± 0.3% | 3.5 ± 0.1% | 5.9 ± 0.2% | 3.4 ± 0.0% |

TABLE 5

| | PQ15/CordapA | | PQ15 | | PQ71/CordapA | | PQ71 | | CordapA | | Control | |
|---|---|---|---|---|---|---|---|---|---|---|---|---|
| | Em | En | Em | En | Em | En | Em | En | Em | En | Em | En |
| Ala | 343 ± 28 | 61 ± 1 | 740 ± 4 | 119 ± 14 | 350 ± 2 | 41 ± 8 | 622 ± 7 | 57 ± 8 | 307 ± 19 | 39 ± 4 | 629 ± 33 | 41 ± 1 |
| Arg | 488 ± 63 | 27 ± 2 | 344 ± 5 | 46 ± 2 | 520 ± 50 | 20 ± 2 | 392 ± 96 | 23 ± 6 | 412 ± 26 | 18 ± 4 | 279 ± 57 | 19 ± 1 |
| Asn | 1220 ± 172 | 109 ± 2 | 2419 ± 172 | 203 ± 5 | 1074 ± 118 | 88 ± 19 | 1893 ± 392 | 180 ± 68 | 809 ± 31 | 49 ± 10 | 1130 ± 87 | 63 ± 3 |
| Asp | 113 ± 25 | 257 ± 23 | 158 ± 32 | 350 ± 69 | 207 ± 63 | 177 ± 29 | 237 ± 34 | 226 ± 44 | 117 ± 6 | 91 ± 13 | 218 ± 56 | 72 ± 1 |
| Glu | 337 ± 45 | 122 ± 1 | 672 ± 65 | 240 ± 38 | 397 ± 115 | 99 ± 23 | 445 ± 40 | 151 ± 60 | 297 ± 6 | 69 ± 8 | 573 ± 105 | 65 ± 8 |
| Gln | 100 ± 28 | 27 ± 2 | 103 ± 2 | 57 ± 6 | 102 ± 10 | 21 ± 4 | 90 ± 36 | 46 ± 26 | 124 ± 18 | 15 ± 1 | 95 ± 26 | 18 ± 1 |
| Gly | 65 ± 4 | 12 ± 0 | 88 ± 10 | 19 ± 1 | 67 ± 4 | 10 ± 1 | 91 ± 10 | 13 ± 1 | 66 ± 3 | 9 ± 1 | 103 ± 18 | 11 ± 1 |
| His | 166 ± 15 | 21 ± 1 | 139 ± 1 | 27 ± 1 | 169 ± 16 | 14 ± 1 | 157 ± 9 | 19 ± 4 | 179 ± 12 | 12 ± 3 | 143 ± 8 | 15 ± 1 |
| Ile | 83 ± 33 | 10 ± 0 | 116 ± 62 | 17 ± 2 | 84 ± 35 | 8 ± 1 | 91 ± 40 | 9 ± 1 | 102 ± 21 | 8 ± 2 | 119 ± 14 | 8 ± 1 |
| Leu | 81 ± 4 | 13 ± 1 | 51 ± 6 | 25 ± 2 | 73 ± 15 | 9 ± 2 | 38 ± 3 | 13 ± 2 | 79 ± 13 | 7 ± 1 | 41 ± 15 | 8 ± 1 |
| Lys | 23159 ± 2325 | 119 ± 7 | 302 ± 102 | 28 ± 1 | 21581 ± 1085 | 105 ± 28 | 431 ± 175 | 20 ± 5 | 16630 ± 1070 | 58 ± 4 | 238 ± 70 | 10 ± 3 |
| Met | 46 ± 6 | 6 ± 1 | 0 ± 0 | 11 ± 2 | 63 ± 9 | 3 ± 4 | 45 ± 9 | 6 ± 2 | 29 ± 41 | 3 ± 4 | 23 ± 32 | 4 ± 0 |
| Phe | 29 ± 40 | 14 ± 1 | 28 ± 40 | 23 ± 4 | 34 ± 48 | 10 ± 1 | 18 ± 25 | 12 ± 3 | 0 ± 0 | 10 ± 2 | 33 ± 46 | 8 ± 1 |
| Ser | 148 ± 7 | 25 ± 1 | 286 ± 21 | 57 ± 3 | 141 ± 11 | 18 ± 5 | 276 ± 56 | 25 ± 3 | 139 ± 8 | 17 ± 5 | 290 ± 13 | 19 ± 1 |
| Thr | 41 ± 2 | 13 ± 1 | 93 ± 11 | 36 ± 4 | 28 ± 39 | 11 ± 2 | 94 ± 10 | 18 ± 3 | 42 ± 0 | 8 ± 2 | 89 ± 9 | 10 ± 2 |
| Trp | 100 ± 2 | 9 ± 2 | 35 ± 49 | 13 ± 0 | 111 ± 23 | 8 ± 1 | 82 ± 1 | 10 ± 2 | 93 ± 18 | 3 ± 4 | 90 ± 28 | 7 ± 1 |
| Tyr | 251 ± 6 | 29 ± 1 | 176 ± 1 | 60 ± 5 | 411 ± 103 | 31 ± 11 | 214 ± 23 | 45 ± 7 | 307 ± 12 | 17 ± 6 | 220 ± 44 | 18 ± 1 |
| Val | 110 ± 4 | 17 ± 0 | 139 ± 18 | 33 ± 6 | 109 ± 11 | 12 ± 2 | 109 ± 13 | 17 ± 3 | 107 ± 11 | 12 ± 0 | 123 ± 2 | 12 ± 1 |
| Total | 26874 ± 1932 | 885 ± 28 | 5884 ± 85 | 1359 ± 127 | 25516 ± 1455 | 679 ± 89 | 5321 ± 798 | 886 ± 247 | 19835 ± 882 | 442 ± 71 | 4430 ± 682 | 403 ± 25 |
| AAA | 581 ± 9 | 8 ± 0 | 12 ± 17 | 8 ± 0 | 418 ± 41 | 6 ± 1 | 0 ± 0 | 4 ± 1 | 635 ± 98 | 6 ± 1 | 44 ± 31 | 2 ± 0 |
| Sac | 3937 ± 14 | 116 ± 3 | 95 ± 13 | 13 ± 1 | 3682 ± 631 | 91 ± 15 | 52 ± 73 | 11 ± 1 | 3625 ± 288 | 85 ± 9 | 249 ± 177 | 13 ± 4 |

As shown in Table 5, results from the dissected embryo and endosperm tissue were similar to the data from the analysis of whole kernels. F1 materials harboring CordapA had increases in lysine and lysine metabolites, and the zein reduction F1s had higher asparagine, aspartate, and glutamate. In general, free amino acids were more concentrated (in ppm) in the embryo, which led to an amplification of some of the minor differences which would otherwise have been statistically insignificant when examined across intact kernels. For example, the expression of CordapA also reduced alanine and serine by approximately 50% in embryo tissues (comparing PQ15/CordapA, PQ71/CordapA and CordapA to PQ15, PQ71 and Control). On the other hand, most of increases of asparagine, aspartate, and glutamate in zein reduction lines were found in the endosperm (comparing PQ15 and PQ71 to Control).

Dissected Embryo and Endosperm-Total Amino Acid Analysis

The total amino acid analysis results for dissected embryos and endosperms are given in Table 6, with the data parts per million (ppm) and presented as averages of two plots plus or minus a standard deviation. Asparagine and aspartate are combined ("Asx"); glutamine and glutamate are combined ("Glx").

TABLE 6

| | | PQ15/CordapA | | PQ15 | | PQ71/CordapA | | PQ71 | |
|---|---|---|---|---|---|---|---|---|---|
| | | Em | En | Em | En | Em | En | Em | En |
| | Ala | 10759 ± 120 | 5775 ± 64 | 11570 ± 0 | 6145 ± 21 | 10790 ± 184 | 7540 ± 354 | 12090 ± 311 | 8880 ± 877 |
| | Arg | 16020 ± 693 | 3085 ± 78 | 15745 ± 205 | 3380 ± 113 | 17240 ± 240 | 3530 ± 42 | 17860 ± 1541 | 4265 ± 375 |

TABLE 6-continued

| | | | | | | | | |
|---|---|---|---|---|---|---|---|---|
| Asx | 12660 ± 14 | 4825 ± 7 | 14190 ± 170 | 5320 ± 184 | 13220 ± 240 | 5780 ± 212 | 15260 ± 1329 | 6955 ± 841 |
| Glx | 25315 ± 106 | 15385 ± 134 | 26360 ± 212 | 16720 ± 14 | 25705 ± 460 | 20985 ± 1054 | 27975 ± 1619 | 25190 ± 2659 |
| Gly | 9900 ± 141 | 2750 ± 14 | 9770 ± 127 | 2975 ± 106 | 10225 ± 120 | 3125 ± 64 | 10740 ± 495 | 3615 ± 290 |
| His | 5785 ± 78 | 1355 ± 219 | 4915 ± 191 | 1685 ± 120 | 6005 ± 35 | 1825 ± 21 | 5340 ± 212 | 2485 ± 134 |
| Ile | 5270 ± 28 | 2555 ± 7 | 5545 ± 35 | 2710 ± 14 | 5365 ± 148 | 3315 ± 106 | 5825 ± 78 | 3920 ± 396 |
| Leu | 11855 ± 35 | 9095 ± 106 | 12505 ± 148 | 9695 ± 35 | 11740 ± 240 | 12460 ± 636 | 12875 ± 163 | 14730 ± 1570 |
| Lys | 34690 ± 2291 | 2030 ± 14 | 9895 ± 92 | 2060 ± 99 | 33415 ± 686 | 2220 ± 14 | 10970 ± 636 | 2365 ± 233 |
| Phe | 5785 ± 92 | 2835 ± 21 | 6130 ± 14 | 2990 ± 14 | 5840 ± 156 | 3620 ± 127 | 6575 ± 262 | 4330 ± 396 |
| Ser | 8645 ± 233 | 3730 ± 71 | 8665 ± 134 | 3985 ± 78 | 8940 ± 156 | 4700 ± 198 | 9990 ± 679 | 5555 ± 587 |
| Thr | 6360 ± 28 | 2685 ± 7 | 6600 ± 85 | 2920 ± 71 | 6625 ± 78 | 3345 ± 49 | 7195 ± 134 | 3920 ± 424 |
| Tyr | 5670 ± 42 | 3455 ± 35 | 5850 ± 0 | 3630 ± 99 | 5960 ± 170 | 4250 ± 14 | 6290 ± 184 | 5045 ± 658 |
| Val | 8760 ± 99 | 3720 ± 14 | 9250 ± 14 | 3900 ± 42 | 8980 ± 410 | 4665 ± 148 | 9835 ± 318 | 5445 ± 544 |
| Total | 167510 ± 2376 | 63280 ± 99 | 146990 ± 1131 | 681150 ± 912 | 170050 ± 2546 | 81360 ± 2857 | 158820 ± 7962 | 96700 ± 9984 |
| Lys % | 20.7 ± 1.1% | 3.2 ± 0.0% | 6.7 ± 0.0% | 3.0 ± 0.1% | 19.6 ± 0.1% | 2.7 ± 0.1% | 6.9 ± 0.1% | 2.4 ± 0.0% |

| | Ave ± SD | | | |
|---|---|---|---|---|
| | CordapA | | Control | |
| | Em | En | Em | En |
| Ala | 10180 ± 240 | 6275 ± 290 | 10375 ± 134 | 6930 ± 141 |
| Arg | 16410 ± 735 | 2855 ± 120 | 17290 ± 622 | 3100 ± 57 |
| Asx | 12575 ± 177 | 4415 ± 233 | 12710 ± 552 | 4795 ± 78 |
| Glx | 24405 ± 643 | 16720 ± 764 | 25635 ± 318 | 18630 ± 410 |
| Gly | 9600 ± 255 | 2605 ± 78 | 9530 ± 325 | 2805 ± 21 |
| His | 5770 ± 42 | 1835 ± 163 | 4795 ± 516 | 1971 ± 71 |
| Ile | 4965 ± 120 | 2780 ± 113 | 5005 ± 21 | 3065 ± 92 |
| Leu | 10960 ± 14 | 11325 ± 530 | 11005 ± 163 | 12575 ± 332 |
| Lys | 28020 ± 240 | 1505 ± 49 | 9815 ± 163 | 1525 ± 21 |
| Phe | 5280 ± 127 | 3525 ± 148 | 5425 ± 35 | 3870 ± 85 |
| Ser | 8310 ± 580 | 4080 ± 170 | 8275 ± 205 | 4470 ± 71 |
| Thr | 6405 ± 148 | 2820 ± 141 | 6175 ± 191 | 3060 ± 57 |
| Tyr | 5585 ± 170 | 3740 ± 170 | 5330 ± 85 | 4120 ± 113 |
| Val | 8450 ± 170 | 3535 ± 134 | 8415 ± 247 | 3865 ± 49 |
| Total | 156915 ± 2835 | 68015 ± 3104 | 139780 ± 3140 | 74780 ± 1556 |
| Lys % | 17.9 ± 0.5% | 2.2 ± 0.0% | 7.0 ± 0.0% | 2.0 ± 0.1% |

Comparing PQ15/CordapA to PQ15, PQ71/CordapA to PQ71 and CordapA to Control, the expression of CordapA slightly reduced total amino acid accumulations in endosperm. In the embryo, histidine and lysine were the only amino acids that showed consistent increases in the CordapA containing F1s. With respect to the impact of zein reduction on various total amino acid levels, PQ71, but not PQ15, had higher total amino acid contents compared to Control. However, the increase in total lysine, which occurred only in endosperm, was consistent in both events.

Dissected Embryo and Endosperm-Protein Content and Dry Weight

The protein content and dry weight analysis results-for dissected embryos and endosperms are given in Table 7, presented as means plus or minus confidence intervals (alpha=0.05). Dry weights are given as means of sums of 50 dissected embryo or endosperm in grams.

TABLE 7

| | PQ15/CordapA | | PQ15 | | PQ71/CordapA | | PQ71 | | CordapA | | Control | |
|---|---|---|---|---|---|---|---|---|---|---|---|---|
| | Ave ± CI | | | | | | | | | | | |
| | Em | En | Em | En | Em | En | Em | En | Em | En | Em | En |
| Protein % | 20.59 ± 0.69 | 6.55 ± 0.50 | 18.08 ± 0.48 | 7.62 ± 0.46 | 21.42 ± 0.78 | 8.41 ± 0.86 | 19.45 ± 0.66 | 9.84 ± 0.77 | 18.19 ± 0.48 | 7.02 ± 0.45 | 17.13 ± 0.47 | 7.69 ± 0.67 |
| Dry weight | 1.477 ± 0.097 | 9.717 ± 0.414 | 1.395 ± 0.082 | 9.373 ± 0.471 | 1.470 ± 0.066 | 10.788 ± 0.449 | 1.440 ± 0.073 | 10.863 ± 0.501 | 1.588 ± 0.085 | 11.920 ± 0.530 | 1.643 ± 0.078 | 12.489 ± 0.559 |

In all three pair-wise comparisons, PQ15/CordapA vs. PQ15, PQ71/CordapA vs. PQ71 and CordapA vs. Control, the protein content appeared to increase slightly in the endosperm relative to the embryo, without affecting proportional dry weight. This was consistent with data shown in Table 6, where the total amino acids were higher in embryo tissues and lower in endosperm tissues in materials carrying the CordapA transgene. With respect to the impact of zein reduction, compared to the Control, PQ15 had similar protein contents but significantly reduced weights, while PQ71 had higher protein contents and only small reduction in weights, in both embryo and endosperm.

LKR/SDH Activities of the F1 Developing Kernels

The measured LKR and SDH specific activities in the F1 developing kernels are presented in Table 7. Data are shown as means plus or minus standard deviation (n=3). Each sample was prepared from kernels of a developing ear at 25 days after pollination (DAP), and was assayed in triplicate. Three developing ears per F1 were used. Specific activities for LKR and SDH are reported in nanomoles NADPH oxidized or $NAD^+$ reduced per minute per milligram protein.

TABLE 7

| | PQ15/CordapA | PQ15 | PQ71/CordapA | PQ71 | CordapA | Control |
|---|---|---|---|---|---|---|
| | % ± SD | | | | | |
| LKR | 24.58 ±1.17 | 20.57 ±3.48 | 20.44 ±1.96 | 29.88 ±4.60 | 14.15 ±0.90 | 15.56 ±1.57 |
| SDH | 4.30 ±1.51 | 4.34 ±1.65 | 5.91 ±0.97 | 6.01 ±0.12 | 3.78 ±0.31 | 4.15 ±0.23 |
| LKR/SDH Ratio | 5.72 | 4.74 | 3.46 | 4.97 | 3.74 | 3.75 |

LKR and SDH specific activities in the F1 developing kernels were between 14.15 to 29.88 nanomoles NADPH oxidized per minute per milligram protein and 3.78 to 6.01 $NAD^+$ reduced per minute per milligram protein, respectively. The LKR specific activities were 5- to 10-fold higher than had previously been reported for maize developing endosperm. See, for example, Azevedo et al. (2004) *J. Agric. Food Chem.*, 52:4865-4871, Gaziola et al. (1999) *J. Agric. Food Chem.*, 47:1268-1275, and Kemper et al. (1999) *Plant Cell*, 11:1981-1993, all of which are incorporated by reference herein. Unlike in opaque mutants, the zein reduction by the transgenic approach did not decrease LKR and SDH specificity activities in these F1s. Developing kernels of all the zein reduction F1s (PQ15/CordapA, PQ15, PQ71/CordapA, and PQ71) had similar or higher LKR and SDH specificity activities than those of F1s with normal zein levels, CordapA and Control. The elevated lysine concentration did not appear to increase the LKR and SDH specificity activities (compare PQ15/CordapA to PQ15, PQ71/CordapA to PQ71 and CordapA to Control). The LKR/SDH ratios ranged from 3.46 to 5.72 and were also several fold higher than previously reported, consistent with the accumulation of saccharopine found in high-lysine F1s.

Discussion

The F1 seeds displayed phenotypes similar to homozygous parents. F1 progeny containing the CordapA transgene had higher free lysine (Table 3) and F1 seeds derived from PQ15 and PQ71 showed reduction of zeins (FIG. 3) and elevated total lysine contents (Table 4). Combining zein reduction and CordapA expression, as in the PQ15/CordapA and PQ71/CordapA crosses, resulted in a substantial increase (about a doubling) of the total lysine content observed in the Control material (Table 4).

An unexpected CordapA-dependent synergistic effect on the free lysine accumulation was observed. The CordapA F1 progeny accumulated 1838 ppm free lysine, greater than a 40-fold increase over the Control of 43 ppm (Table 3). Zein reduction synergistically increased free lysine levels derived from CordapA expression, as seen in the combinations of PQ15/CordapA and PQ71/CordapA, which had even higher free lysine content, 2908 and 2498 ppm, respectively. F1s with zein reduction alone (PQ15 and PQ71) had Control levels of free lysine, which indicated that zein reduction enhanced lysine biosynthesis in a synergistic fashion in the presence of CordapA. However, elevated free lysine did not contribute to increases in protein-bound lysine caused by zein reduction. Almost all of the increase in total lysine was found in the endosperm since large amounts of the lysine-poor zeins are reduced in the endosperm of transgenic seeds (Table 6).

It has been proposed that the high lysine content of the opaque-2 mutant (Mertz et al. (1964) *Science*, 145:279-280) is due to the reduction of lysine-poor zeins and a pleiotropic increase in the lysine-rich non-zein proteins. See, for example, Damerval and Devienne (1993) *Heredity*, 70:38-51, Habben et al. (1993) *Plant Mol. Biol.*, 23:825-838, and Lopez-Valenzuela et al. (2004), *Plant Physiol.*, 135:1784-

1797, all of which are incorporated by reference herein. The increases in free lysine caused by zein reduction and CordapA expression in PQ15/CordapA and PQ71/CordapA were calculated from Table 3, yielding calculated free lysine values of 2865 (2908-43) ppm in PQ15/CordapA and 2454 (2498-43) ppm in PQ71/CordapA, respectively. By adding the increases in free lysine to the total lysine of PQ15 and PQ71 shown in Table 4, the expected total lysine contents for PQ15/CordapA and PQ71/CordapA were estimated to be 5975 and 5784 ppm. These estimates were not significantly different from the actual measurements of 6160±354 and 5475±375 ppm (Table 4). Thus, in contrast to earlier hypotheses, higher free lysine did not stimulate the synthesis of lysine-rich non-zein proteins in the transgenic zein reduction lines. Although PQ15 had a protein content similar to Control, its smaller kernels (and thus smaller endosperm) led to it containing less overall protein on a per-kernel basis (Table 2 and Table 7), suggesting that zein reduction in PQ15 had little effect on the synthesis of lysine-rich non-zein proteins. On the other hand, PQ71 has slightly smaller kernels, but a higher protein content and thus the amount of overall protein is comparable to Control (Table 2 and Table 7). All together, the higher total lysine content observed in PQ15 merely reflected zein reduction, while the increase in total lysine content in PQ71 was probably caused by the synthesis of lysine-rich non-zein proteins.

Zein reduction was found to unexpectedly increase the supply of precursor amino acids for CordapA-enhanced lysine biosynthesis, resulting in a synergistic increase in lysine. In the zein reduction F1 is (PQ15 and PQ71), three free amino acids, asparagine, aspartate, and glutamate, had the most noticeable increases among all free amino acids measured (Table 3). The introduction of CordapA to the zein-reduced lines synergistically enhanced lysine biosynthesis and concomitantly reduced asparagine, aspartate, and glutamate (PQ15/CordapA, PQ71/CordapA in Table 2). In plants, lysine is believed to be synthesized from aspartate through the lysine branch of the Asp family pathway; aspartate, in turn, can be synthesized from glutamate or asparagines. See, for example, Galili (2002) *Annu. Rev. Plant Physiol. Plant Mol. Biol.*, 53:27-43, which is incorporated by reference herein. The unexpected changes in aspartate, asparagine and glutamate that were detected in the zein reduction F1s and the zein reduction/CordapA F1s further indicated the importance of these amino acids in enhancing lysine biosynthesis.

Example 2

This non-limiting example describes a recombinant DNA construct useful in introducing sequence for zein reduction into the transgenic plant of the invention, the use of which construct is described generally in U.S. patent application Ser. No. 11/057,062, published as U.S. Patent Application Publication No. 2005/0176670A1 and incorporated by reference in its entirety herein. More specifically, this example describes use of a closed loop of anti-sense-oriented RNA for suppressing at least one zein gene (for example, any one or more of the genes for alpha-, beta-, gamma-, and delta-zeins). The recombinant DNA construct for suppressing at least one zein gene, can include in 5' to 3' order a promoter element operably linked to an anti-sense-oriented DNA element from the at least one zein gene and a sense-oriented DNA element, wherein the sense-oriented DNA element is shorter than the anti-sense-oriented DNA element, and sense-oriented RNA transcribed by the sense-oriented DNA element is complementary to the 5'-most end of anti-sense-oriented RNA transcribed by the anti-sense-oriented RNA transcribed by the anti-sense-oriented DNA element, wherein the transcribed RNA forms a loop of anti-sense-oriented RNA for suppressing the at least one zein gene. In another embodiment, the sequence for zein reduction can be introduced in the transgenic plant of the invention by providing in cells of the transgenic plant a recombinant DNA construct which is transcribed to RNA that forms a loop of anti-sense-oriented RNA for suppressing at least one zein gene.

Example 3

This example describes non-limiting constructs useful in obtaining transgenic maize plants of the invention. Expression cassettes containing heterologous DNA for gene suppression embedded in an intron are described in detail in U.S. Provisional Patent Application No. 60/638,256, and incorporated by reference in its entirety herein. Similar expression cassettes useful in the practice of the present invention are apparent to one versed in the art. For example, a suitable vector useful in obtaining a transgenic plant of the invention includes an expression cassette containing a seed specific promoter and leader, operably linked to an maize heat shock protein intron in which is embedded sequence (such as an inverted repeat of DNA) for suppressing at least one zein synthesis gene, and optionally sequence for suppressing at least one endogenous lysine catabolic enzyme (e.g., maize LKR), followed by targeting sequence and sequence encoding a lysine synthesis gene (e.g., an *E. coli* AKIII, or a *Corynebacterium* DHDPS), and finally DNA with polyadenylation signal and site. The vector can additionally contain a selectable or screenable marker, e.g., a gene encoding glyphosate herbicide resistance.

All of the materials and methods disclosed and claimed herein can be made and used without undue experimentation as instructed by the above disclosure. Although the materials and methods of this invention have been described in terms of preferred embodiments and illustrative examples, it will be apparent to those of skill in the art that variations may be applied to the materials and methods described herein without departing from the concept, spirit and scope of the invention. All such similar substitutes and modifications apparent to those skilled in the art are deemed to be within the spirit, scope and concept of the invention as defined by the appended claims.

What is claimed is:

1. A transgenic maize plant comprising in its genome transgenic DNA encoding an antisense sequence complementary to all or a portion of a 19 kD or 22 kDa alpha-zein messenger RNA (mRNA) and a transgenic DNA for the expression of lysine insensitive aspartate kinase (AK) or dihydrodipicolinic acid synthase (DHDPS), and/or transgenic DNA encoding an antisense sequence complementary to all or a portion of a maize lysine-ketoglutarate reductase (LKR) mRNA and a saccharopine dehydrogenase (SDH) mRNA, whereby expression of said transgenic DNA results in a synergistically increased free lysine content of seed of said transgenic maize plant.

2. The transgenic maize plant of claim 1, wherein said transgenic DNA encodes an antisense sequence complementary to all or a portion of a 19 kD and 22 kDa alpha-zein mRNA.

3. The transgenic maize plant of claim 1, wherein said transgenic maize plant is a progeny transgenic maize plant from genetic crossing of a first parent transgenic maize plant comprising in its genome transgenic DNA encoding an antisense sequence complementary to all or a portion of a 19 kD or 22 kDa alpha-zein mRNA and a second parent transgenic maize plant comprising in its genome transgenic DNA comprising sequence for the expression of lysine insensitive AK or DHDPS, and/or transgenic DNA encoding an antisense sequence complementary to all or a portion of a maize LKR mRNA and a SDH mRNA, wherein said progeny transgenic maize plant from said genetic crossing has in its genome said transgenic DNA encoding an antisense sequence complementary to all or a portion of a 19 kD or 22 kDa alpha-zein mRNA and said transgenic DNA for the expression of lysine insensitive AK or DHDPS, and/or transgenic DNA encoding an antisense sequence complementary to all or a portion of a maize LKR mRNA and a SDH mRNA.

4. A method for providing maize seed with synergistically increased lysine content, comprising: (a) providing a transgenic maize plant comprising in its genome transgenic DNA encoding an antisense sequence complementary to all or a portion of a 19 kD or 22 kDa alpha-zein messenger RNA mRNA and a transgenic DNA for the expression of lysine insensitive aspartate kinase (AK) or dihydrodipicolinic acid synthase (DHDPS), and/or transgenic DNA encoding an antisense sequence complementary to all or a portion of a maize lysine-ketoglutarate reductase (LKR) mRNA and a saccharopine dehydrogenase (SDH) mRNA, (b) expressing said transgenic DNA in seed of said transgenic maize plant, said expressing resulting in a synergistically increased free lysine content of said seed, and (c) harvesting said seed with synergistically increased free lysine content.

5. The method of claim 4, wherein said providing comprises genetic crossing of a first parent transgenic maize plant comprising in its genome transgenic DNA encoding an antisense sequence complementary to all or a portion of a 19 kD or 22 kDa alpha-zein mRNA and a second parent transgenic maize plant comprising in its genome transgenic DNA comprising a sequence for the expression of lysine insensitive AK or DHDPS, and/or transgenic DNA encoding an antisense sequence complementary to all or a portion of a maize LKR mRNA and a SDH mRNA, said genetic crossing resulting in a progeny transgenic maize plant comprising in its genome said transgenic DNA encoding an antisense sequence complementary to all or a portion of a 19 kD or 22 kDa alpha-zein mRNA and said transgenic DNA for the expression of lysine insensitive AK or DHDPS, and/or transgenic DNA encoding an antisense sequence complementary to all or a portion of a maize LKR mRNA and a SDH mRNA.

6. A transgenic maize plant comprising in its genome transgenic DNA comprising in 5' to 3' order
  a) a promoter element operably linked to an anti-sense oriented DNA element complementary to all or a portion of a 19 kD or 22 kDa alpha-zein mRNA and a sense-oriented DNA, wherein the sense-oriented DNA element is shorter than the anti-sense-oriented DNA element complementary to all or a portion of a 19 kD or 22 kDa alpha-zein mRNA and the sense-oriented RNA transcribed by the sense-oriented DNA is complementary to the 5'-most end of anti-sense oriented RNA transcribed by the anti-sense oriented RNA transcribed by the anti-sense-oriented DNA element, wherein the transcribed RNA forms a loop of anti-sense oriented RNA for suppressing the at least one zein gene; and
  b) a transgenic DNA encoding a polypeptide with lysine-insensitive aspartate kinase (AK) activity or dihydrodipicolinic acid synthase (DHDPS) activity, and/or an antisense sequence complementary to all or a portion of maize lysine-ketoglutarate reductase (LKR) mRNA and saccharopine dehydrogenase (SDH) mRNA, whereby expression of said transgenic DNA results in a synergistically increased free lysine content of seed of said transgenic maize plant.

7. A seed of a transgenic maize plant according to claim 1, wherein the seed comprises transgenic DNA encoding an antisense sequence complementary to all or a portion of a 19 kD or 22 kDa alpha-zein mRNA, a sequence for the expression of lysine insensitive aspartate kinase (AK) or dihydrodipicolinic acid synthase (DHDPS), and/or transgenic DNA encoding an antisense sequence complementary to all or a portion of a maize LKR mRNA and a SDH mRNA.

8. A corn meal or flour from a seed of a transgenic maize plant according to claim 1, wherein the corn meal or flour comprises transgenic DNA encoding an antisense sequence complementary to all or a portion of a 19 kD or 22 kDa alpha-zein mRNA, a sequence for the expression of lysine insensitive aspartate kinase (AK) or dihydrodipicolinic acid synthase (DHDPS), and/or transgenic DNA encoding an antisense sequence complementary to all or a portion of a maize LKR mRNA and a SDH mRNA.

* * * * *

UNITED STATES PATENT AND TRADEMARK OFFICE
CERTIFICATE OF CORRECTION

| | | |
|---|---|---|
| PATENT NO. | : 7,683,237 B2 | Page 1 of 1 |
| APPLICATION NO. | : 11/077089 | |
| DATED | : March 23, 2010 | |
| INVENTOR(S) | : Kriz et al. | |

It is certified that error appears in the above-identified patent and that said Letters Patent is hereby corrected as shown below:

In claim 1, column 26, line 49, delete "19 kD" and insert --19 kDa--.

In claim 2, column 26, line 61, delete "19 kD" and insert --19 kDa--.

In claim 3, column 26, line 67, delete "19 kD" and insert --19 kDa--.

In claim 3, column 27, line 9, delete "19 kD" and insert --19 kDa--.

In claim 4, column 27, line 19, delete "19 kD" and insert --19 kDa--.

In claim 5, column 27, line 34, delete "19 kD" and insert --19 kDa--.

In claim 5, column 27, line 43, delete "19 kD" and insert --19 kDa--.

In claim 6, column 28, line 7, delete "19 kD" and insert --19 kDa--.

In claim 6, column 28, line 10, delete "19 kD" and insert --19 kDa--.

In claim 6, column 28, line 17, delete "the at least" and insert --at least--.

In claim 7, column 28, line 30, delete "kD or" and insert --kDa or--.

In claim 8, column 28, line 38, delete "19 kD" and insert --19 kDa--.

Signed and Sealed this
Thirteenth Day of September, 2011

David J. Kappos
*Director of the United States Patent and Trademark Office*